USO11446145B2

(12) United States Patent
Crosbie et al.

(10) Patent No.: US 11,446,145 B2
(45) Date of Patent: Sep. 20, 2022

(54) DELIVERY DEVICE HAVING A CAPSULE FOR DELIVERING A PROSTHESIS AND A PULL WIRE FOR STEERING THE CAPSULE

(71) Applicant: MEDTRONIC, INC., Minneapolis, MN (US)

(72) Inventors: Niall Crosbie, Clare CE (IE); Constantin Ciobanu, County Galway (IE); Tomas Gilson, Galway (IE); Nicholas Fox, Oranmore (IE)

(73) Assignee: MEDTRONIC, INC., Minneapolis, MN (US)

( * ) Notice: Subject to any disclaimer, the term of this patent is extended or adjusted under 35 U.S.C. 154(b) by 233 days.

(21) Appl. No.: 16/935,603

(22) Filed: Jul. 22, 2020

(65) Prior Publication Data

US 2021/0022859 A1 Jan. 28, 2021

Related U.S. Application Data

(60) Provisional application No. 62/878,378, filed on Jul. 25, 2019.

(51) Int. Cl.
*A61F 2/24* (2006.01)
(52) U.S. Cl.
CPC .......... *A61F 2/2436* (2013.01); *A61F 2/2418* (2013.01); *A61F 2210/0014* (2013.01)
(58) Field of Classification Search
CPC .................. A61F 2/2436; A61F 2/2418; A61F 2210/0014; A61F 2002/9623;

(Continued)

(56) References Cited

U.S. PATENT DOCUMENTS 4,686,963 A * 8/1987 Cohen .................. A61B 1/0055
138/120
8,226,710 B2 7/2012 Nguyen et al.
(Continued)

FOREIGN PATENT DOCUMENTS

EP 2480167 A1 8/2012

OTHER PUBLICATIONS

PCT/US2020/043228, The International Search Report and Written Opinion, dated Oct. 27, 2020, 12 pages.

*Primary Examiner* — Kelly J Bekker
*Assistant Examiner* — Andrew P. Restaino
(74) *Attorney, Agent, or Firm* — Medler Ferro Woodhouse & Mills PLLC

(57) ABSTRACT

A delivery device includes a handle, a sheath distally extending from the handle, a capsule distally extending from the sheath, and a pull wire having a proximal end attached to the handle and a distal end attached to the capsule. The sheath defines a central lumen there-through and has a longitudinally-extending lumen formed within a wall of the sheath. The capsule has a tubular body with an intermediate region having a plurality of ribs and a plurality of slots defined therein. The capsule includes an indented segment defined on the tubular body, the indented segment being disposed radially inward relative to the tubular body. The pull wire is tensioned to bend the capsule. The pull wire is slidably disposed within the longitudinally-extending lumen of the sheath and along an inner surface of the tubular body of the capsule with a portion of the pull wire crossing over an outer surface of the indented segment.

19 Claims, 18 Drawing Sheets

(58) Field of Classification Search
CPC .............. A61F 2250/0018; A61F 2/966; A61F
2002/9505; A61F 2/2412; A61F 2/2427;
A61F 2220/005; A61F 2230/0054; A61F
2002/9528; A61F 2230/008; A61F
2230/0067; A61F 2002/9534
See application file for complete search history.

(56) References Cited

U.S. PATENT DOCUMENTS

| | | |
|---|---|---|
| 8,562,673 B2 | 10/2013 | Yeung et al. |
| 8,579,963 B2 | 11/2013 | Tabor |
| 8,974,524 B2 | 3/2015 | Yeung et al. |
| 10,278,852 B2 | 5/2019 | Griffin |
| 2014/0222142 A1 | 8/2014 | Kovalsky et al. |
| 2014/0343670 A1 | 11/2014 | Bakis et al. |
| 2017/0281344 A1 | 10/2017 | Costello |

\* cited by examiner

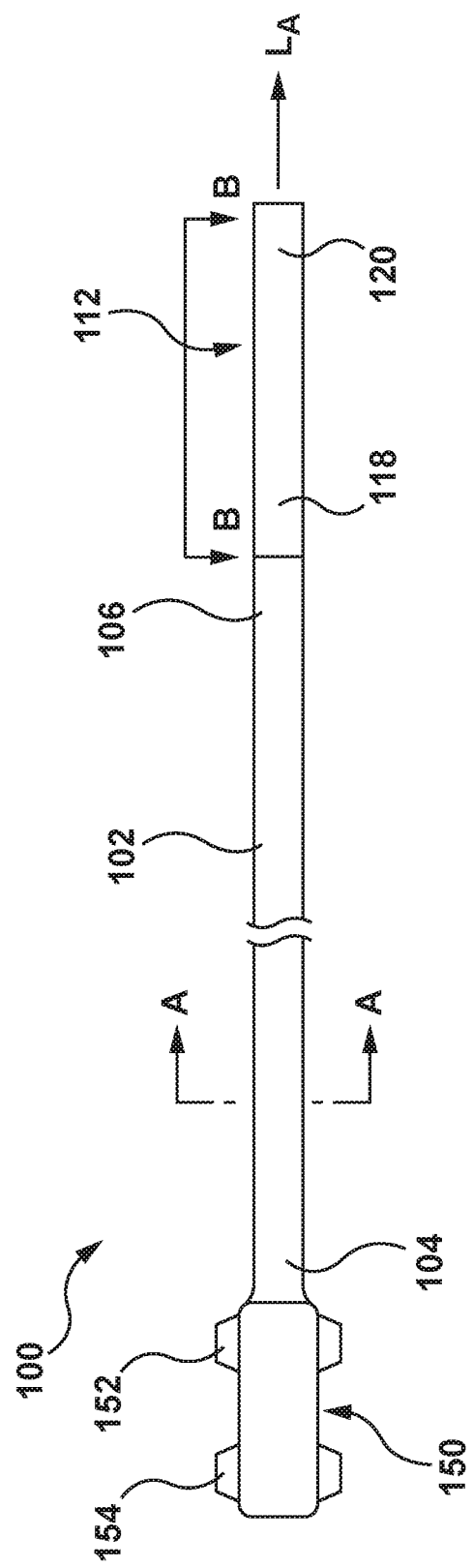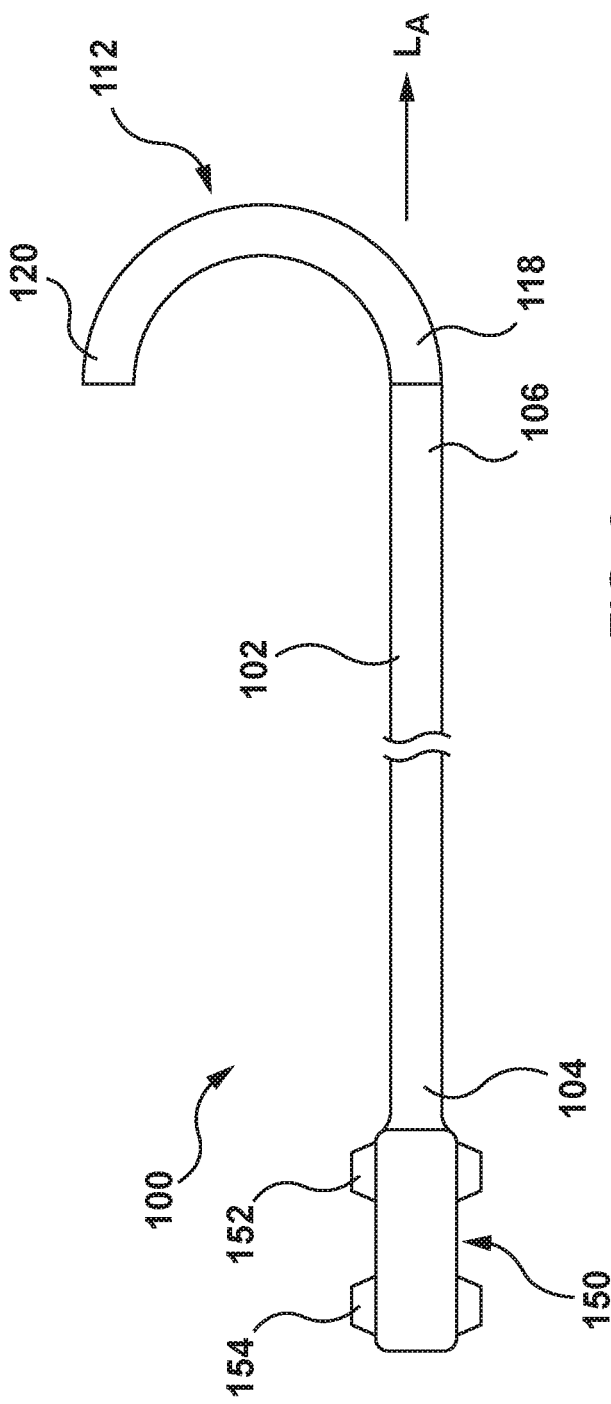

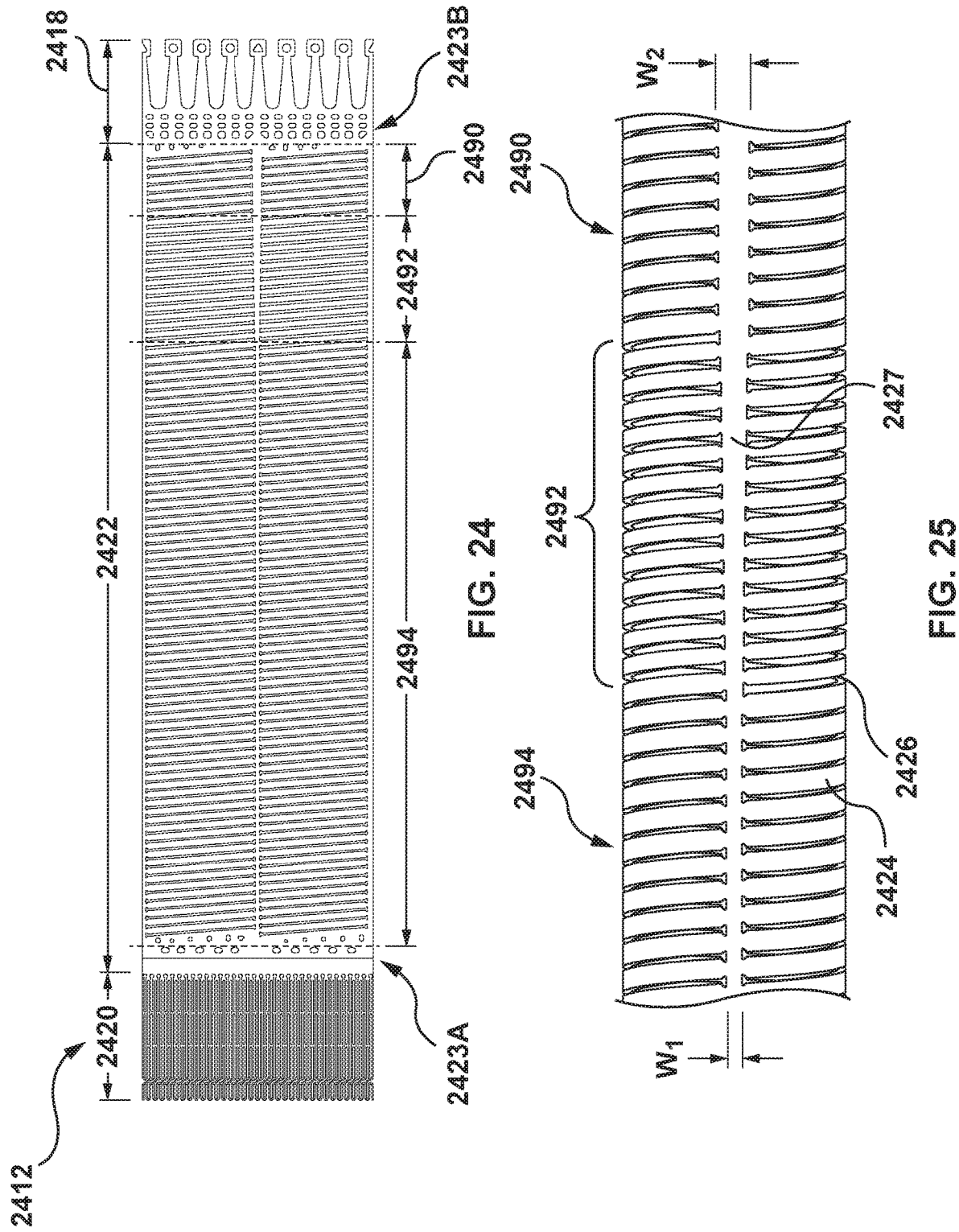

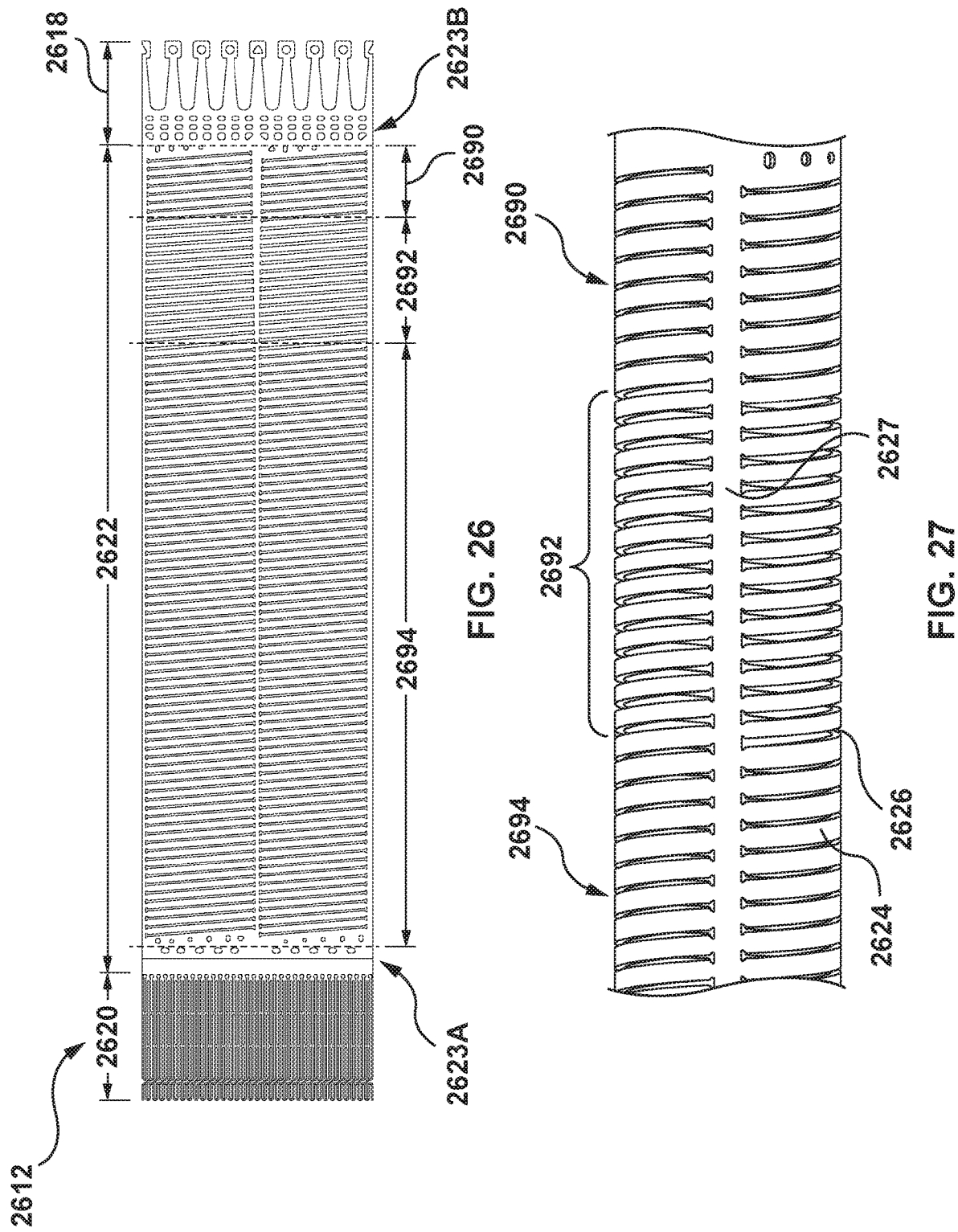

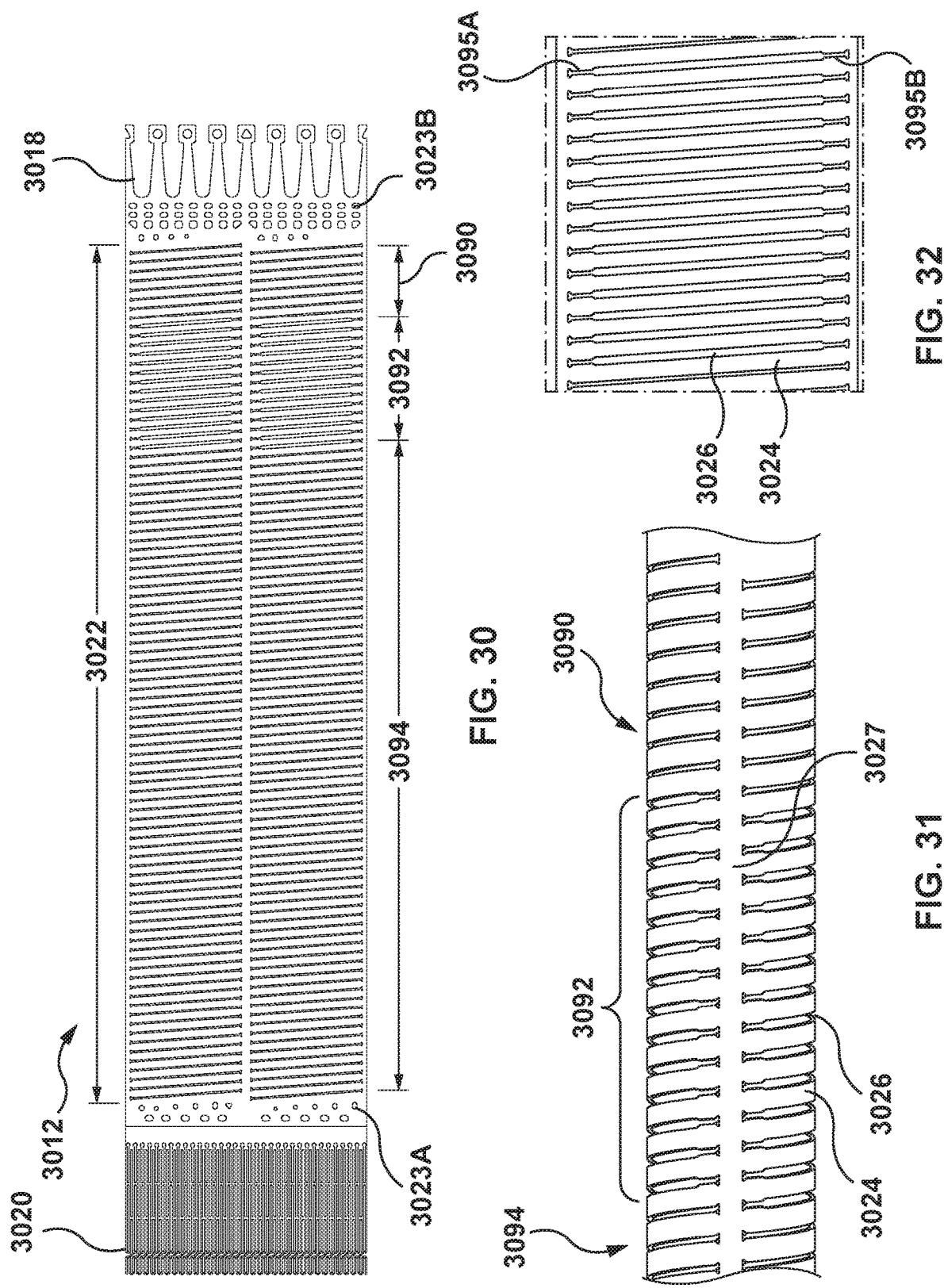

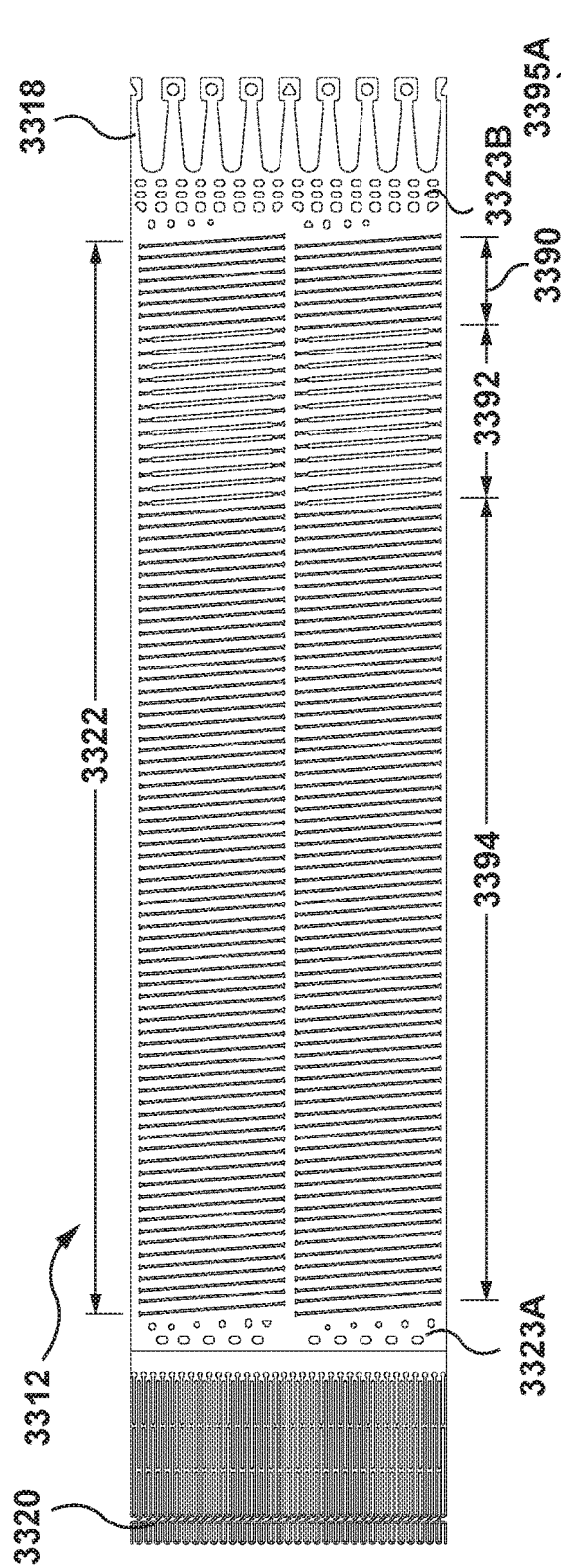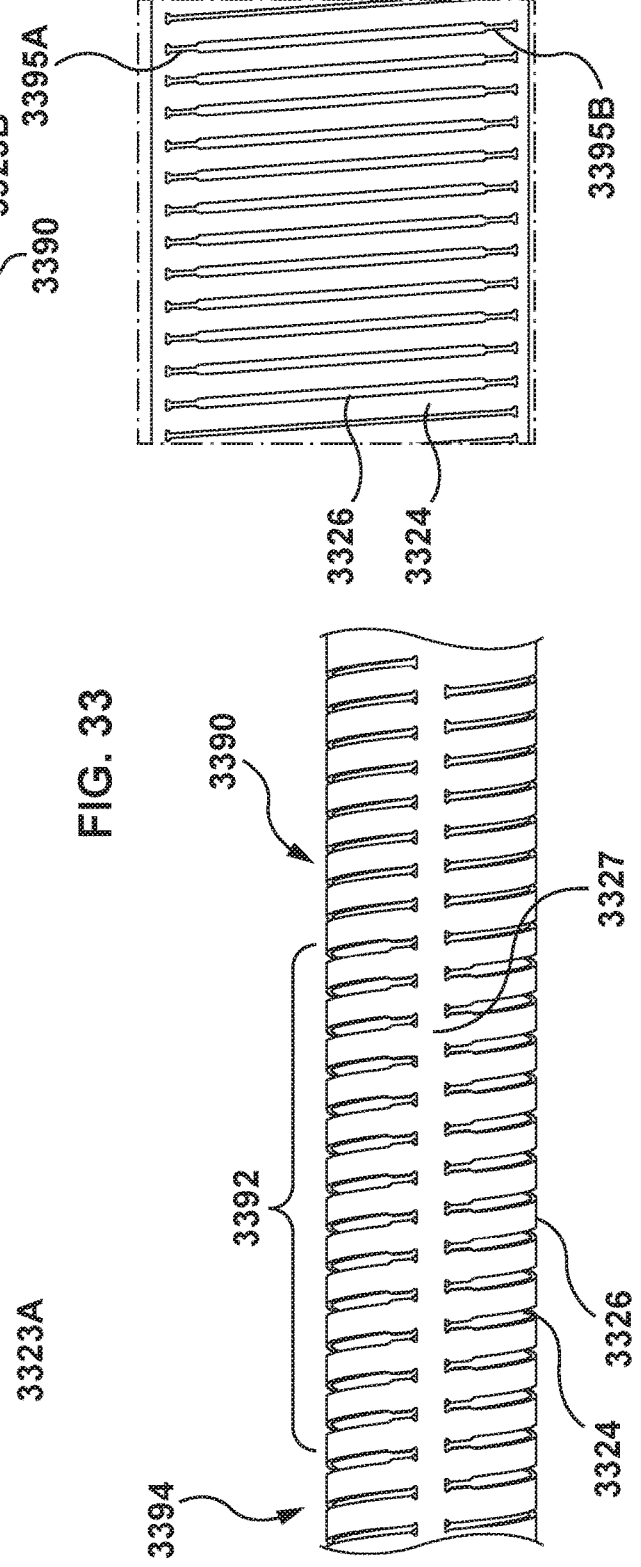
FIG. 33
FIG. 34
FIG. 35

DELIVERY DEVICE HAVING A CAPSULE FOR DELIVERING A PROSTHESIS AND A PULL WIRE FOR STEERING THE CAPSULE

CROSS-REFERENCE TO RELATED APPLICATIONS

This application claims the benefit of U.S. Provisional Patent Application Ser. No. 62/878,378, filed Jul. 25, 2019, which is hereby incorporated by reference in its entirety for all purposes.

FIELD OF THE INVENTION

The present invention relates to systems for percutaneous transcatheter delivery and implantation of a prosthesis, such as a stent, a stent-graft or a prosthetic valve. More particularly, the present invention relates to a delivery device including a capsule for delivery of the prosthesis and a pull wire for steering the capsule.

BACKGROUND OF THE INVENTION

Among medical catheters commonly used to access vascular and other locations within a body and to perform various functions at those locations are medical catheters, or delivery catheters, adapted to deliver and deploy medical devices such as prosthetic heart valves, stent-grafts, and stents to selected targeted sites in the body. Such medical devices typically are releasably carried within a distal region of the delivery catheter in a radially compressed delivery state as the catheter is navigated to and positioned at a target treatment/deployment site. In many cases, such as those involving cardiovascular vessels, the route to the treatment/deployment site may be tortuous and may present conflicting design considerations requiring compromises between dimensions, flexibilities, material selection, operational controls and the like.

Typically advancement of a delivery catheter within a patient is monitored fluoroscopically to enable a clinician to manipulate the catheter to steer and guide its distal end through the patient's vasculature to the target treatment/deployment site. This tracking requires a distal end of the delivery catheter to be able to navigate safely to the target treatment/deployment site through manipulation of a proximal end by the clinician. Such manipulation may encompass pushing, retraction and torque forces or a combination of all three. It is therefore required for the distal end of the delivery catheter to be able to withstand all these force.

A delivery catheter desirably will have a low profile/small outer diameter to facilitate navigation through tortuous vasculature; however, small outer diameter catheters present various design difficulties resulting from competing considerations, resulting in design trade-offs. For instance, such delivery catheters must be flexible enough to navigate the tortuous vasculature or anatomy of a patient. However, typical constructions of delivery catheters must attempt to balance a requisite flexibility, with axial strength/stiffness (the property that permits the delivery catheter to be pushed and pulled), and torsional strength/stiffness (the property that permits the delivery catheter to be rotated about its longitudinal axis). It is especially important to balance these properties in a distal portion of the delivery catheter within which a prosthesis is held in its compressed, delivery state.

A need in the art still generally exists for improved apparatus and methods for navigating through or within a patient's anatomy.

BRIEF SUMMARY OF THE INVENTION

Embodiments hereof relate to a delivery device that includes a handle, a sheath distally extending from the handle, a capsule distally extending from the sheath, and a pull wire having a proximal end attached to the handle and a distal end attached to the capsule. The sheath defines a central lumen there-through and has a longitudinally-extending lumen formed within a wall of the sheath. The capsule has a tubular body with an intermediate region having a plurality of ribs and a plurality of slots defined therein. The capsule includes an indented segment defined on the tubular body, the indented segment being disposed radially inward relative to the tubular body. The pull wire is tensioned to bend the capsule. The pull wire is slidably disposed within the longitudinally-extending lumen of the sheath and along an inner surface of the tubular body of the capsule with a portion of the pull wire crossing over an outer surface of the indented segment.

Embodiments hereof also relate to a delivery system for transcatheter delivery of a prosthesis includes a delivery device and a prosthesis. The delivery device includes a handle, a sheath distally extending from the handle, a capsule distally extending from the sheath, and a pull wire having a proximal end attached to the handle and a distal end attached to the capsule. The sheath defines a central lumen there-through and has a longitudinally-extending lumen formed within a wall of the sheath. The capsule has a tubular body with an intermediate region having a plurality of ribs and a plurality of slots defined therein. The capsule includes an indented segment defined on the tubular body, the indented segment being disposed radially inward relative to the tubular body. The pull wire is tensioned to bend the capsule. The pull wire is slidably disposed within the longitudinally-extending lumen of the sheath and along an inner surface of the tubular body of the capsule with a portion of the pull wire crossing over an outer surface of the indented segment. The prosthesis is configured to be disposed within the capsule of the sheath in a radially compressed delivery state and configured to deploy to an expanded state after release from the capsule of the sheath Embodiments hereof also relate to a method of delivering and deploying a prosthesis at a treatment site. A delivery system is advanced through the vasculature to the treatment site. The delivery system includes a delivery device and a prosthesis. The delivery device includes a handle, a sheath distally extending from the handle, a capsule distally extending from the sheath, and a pull wire having a proximal end attached to the handle and a distal end attached to the capsule. The sheath defines a central lumen there-through and has a longitudinally-extending lumen formed within a wall of the sheath, The capsule has a tubular body with an intermediate region having a plurality of ribs and a plurality of slots defined therein. The capsule includes an indented segment defined on the tubular body, the indented segment being disposed radially inward relative to the tubular body. The prosthesis is disposed in the capsule of the sheath in a compressed delivery state. The pull wire is slidably disposed within the longitudinally-extending lumen of the sheath and along an inner surface of the tubular body of the capsule with a portion of the pull wire crossing over an outer surface of the indented segment. The pull wire is tensioned in order to bend the capsule. The capsule is retracted to deploy the prosthesis to an expanded deployed state at the treatment site.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 1 is a side view of a delivery system according to an embodiment hereof, wherein the delivery system includes a capsule and the capsule is shown in a non-bent configuration.

FIG. 2 is a side view of the delivery system of FIG. 1, wherein the capsule is shown in a bent configuration.

FIG. 24 is a side view of a capsule according to another embodiment hereof, wherein the capsule includes an alternative cut pattern.

FIG. 25 is a perspective view of a portion of the capsule of FIG. 24.

FIG. 26 is a side view of a capsule according to another embodiment hereof, wherein the capsule includes an alternative cut pattern.

FIG. 27 is a perspective view of a portion of the capsule of FIG. 26.

FIG. 30 is a side view of a capsule according to another embodiment hereof, wherein the capsule includes an alternative cut pattern.

FIG. 31 is a perspective view of a portion of the capsule of FIG. 30.

FIG. 32 is a flattened view of a portion of the capsule of FIG. 30.

FIG. 33 is a side view of a capsule according to another embodiment hereof, wherein the capsule includes an alternative cut pattern.

FIG. 34 is a perspective view of a portion of the capsule of FIG. 33.

FIG. 35 is a flattened view of a portion of the capsule of FIG. 33.

DETAILED DESCRIPTION OF THE INVENTION

Figure 1A:
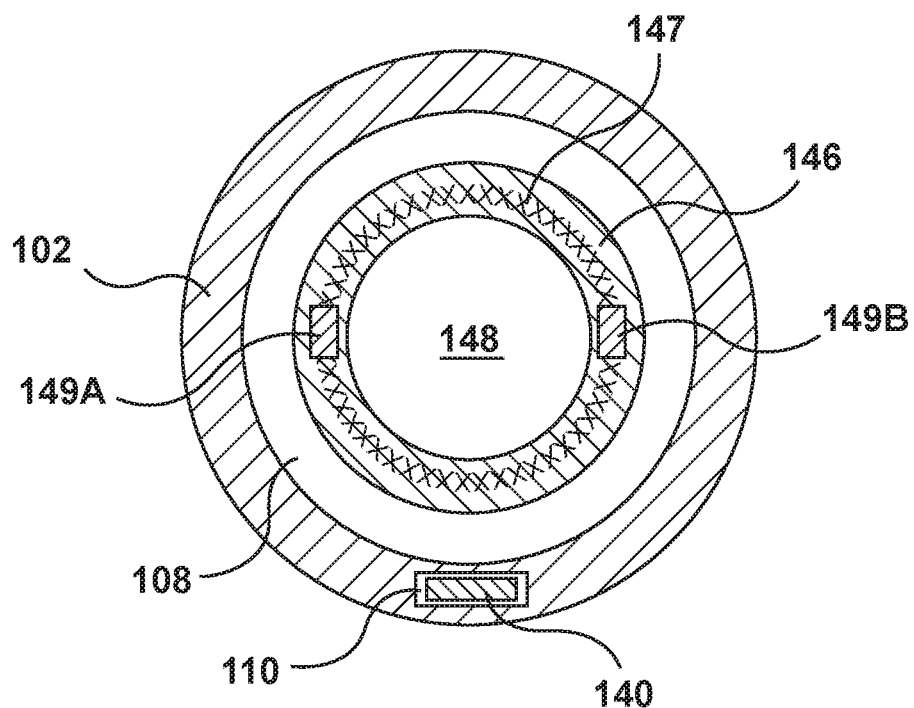
FIG. 1A is a cross-sectional view taken along line A-A of FIG. 1.

Specific embodiments of the present invention are now described with reference to the figures, wherein like reference numbers indicate identical or functionally similar elements. The terms "distal" and "proximal", when used in the following description to refer to a sheath, a delivery device, or a catheter-based delivery system are with respect to a position or direction relative to the treating clinician. Thus, "distal" and "distally" refer to positions distant from, or in a direction away from the treating clinician, and the terms "proximal" and "proximally" refer to positions near, or in a direction toward the treating clinician. The terms "distal" and "proximal", when used in the following description to refer to a device to be implanted into a vessel, such as a heart valve prosthesis, are used with reference to the direction of blood flow from the heart. Thus, "distal" and "distally" refer to positions in a downstream direction with respect to the direction of blood flow, and the terms "proximal" and "proximally" refer to positions in an upstream direction with respect to the direction of blood flow.

The following detailed description is merely exemplary in nature and is not intended to limit the invention or the application and uses of the invention. Furthermore, there is no intention to be bound by any expressed or implied theory presented in the preceding technical field, background, brief summary, or the following detailed description.

Embodiments hereof relate to a delivery device 100 for delivering a prosthesis 101. The prosthesis 101 is held or disposed in a radially compressed delivery state within a capsule 112 of the delivery device 100. The delivery device 100 is configured to retain the prosthesis 101 in the radially compressed state for delivery to a treatment site, such as a native aortic valve or a native mitral valve. The delivery device 100 is further configured to release the prosthesis 101 at a treatment site and the prosthesis 101 is configured to deploy to an expanded state after release from the capsule 112. It should be understood that the prosthesis 101 described herein is shown by way of example and not limitation and that any other prosthesis may be suitably delivered by the delivery device 100 in accordance with embodiments hereof.

The delivery device 100 includes a tubular component or sheath 102 and a handle 150 coupled to and proximally extending from a proximal end 104 of the sheath 102. The sheath 102 has a distal end 106 opposite the handle 150, and a proximal end 118 of the capsule 112 is attached to the distal end 106 of the sheath 102 such that the capsule 112 distally extends from the sheath 102. FIG. 1 is a side view of the delivery device 100 with the capsule 112 in a straight or non-bent configuration, while FIG. 2 is a side view of the delivery device 100 with the capsule 112 in a curved or bent configuration. More particularly, a pull wire 140 (not shown in FIGS. 1 and 2) has a proximal end 142 attached to the handle 150 and a distal end 144 attached to the capsule 112. The pull wire 140 is selectively tensioned by the user to bend the capsule 112 to the curved or bent configuration of FIG. 2. The dimension of the curvature of the capsule 112 in the curved or bent configuration depends upon the target anatomy for use of the delivery device 100, and/or the size or profile of the delivery device 100. In an embodiment in which the delivery device 100 is utilized in a TAVI or transcatheter aortic valve implantation procedure, the radius of curvature of the capsule 112 in the curved or bent configuration ranges between twenty (20) millimeters and sixty (60) millimeters.

The sheath 102 may be formed of one or more polymeric materials, non-exhaustive examples of which include polyethylene, polyethylene block amide copolymer (PEBA), polyamide and/or combinations thereof, either laminated, blended or co-extruded. Optionally, the sheath 102 or some portion thereof may be formed as a composite having a reinforcement layer incorporated within a polymeric body in order to enhance strength and/or flexibility and/or torquability. Suitable reinforcement layers include braiding, wire mesh layers, embedded axial wires, embedded helical or circumferential wires, hypotubes, and the like. In one embodiment, for example, at least a proximal portion of the sheath 102 may be formed from a reinforced polymeric tube.

As best shown on FIG. 1A, which is a cross-sectional view of the sheath 102 of FIG. 1 taken along line A-A of FIG. 1, the sheath 102 defines a central lumen 108 extending there-through, i.e., from the proximal end 104 to the distal end 106 thereof, and a longitudinally-extending lumen 110 is formed with a wall of the sheath 102 and extends from the proximal end 104 to the distal end 106 thereof. In an embodiment, the longitudinally-extending lumen 110 is preformed in the wall of the sheath 102 and may be formed for example by multi-lumen profile extrusion. The central lumen 108 is sized or configured to house an inner shaft 146, while the longitudinally-extending lumen 110 houses the pull wire 140. In embodiments hereof, the longitudinally-extending lumen 110 may have an oblong cross-section in order to accommodate the pull wire 140, which may have a flat or flattened longitudinal profile. In another embodiment (not shown), the longitudinally-extending lumen 110 as well as the pull wire 140 disposed there-through may have different configurations or shapes including oval or circular. The pull wire 140 is slidably disposed within the longitudinally-extending lumen 110 such that it may be selectively tensioned by the user to bend the capsule 112. As used herein, "slidably" denotes back and forth movement in a longitudinal direction along or generally parallel to a central longitudinal axis LA of the delivery device 100. While the pull wire 140 is primarily housed or disposed within the longitudinally-extending lumen 110 of the sheath 102, the proximal end 142 proximally extends beyond the proximal end 104 of the sheath 102 and is accessible via the handle 150 to be pulled or pushed which results in controlled bending movement of the capsule 112.

As also shown on FIG. 1A, the sheath 102 is slidably disposed over the inner shaft 146. The inner shaft 146 is a tubular component defining a central lumen 148 therethrough. In an embodiment, the central lumen 148 may be configured to slidably receive a guidewire (not shown) therethrough. A proximal end (not shown) of the inner shaft 146 is attached or secured within the handle 150. In an embodiment, the inner shaft 146 is longitudinally reinforced with one or more axial wires 149A, 149B. More particularly, the inner shaft 146 is formed of a polymer material such as polyethylene, polyethylene block amide copolymer (PEBA), polyamide, or nylon, that encapsulates a braid 147 as well as the axial wires 149A, 149B that are disposed at circumferentially opposite locations. The braid 147 can be a conventional metal braid (e.g., stainless steel braiding) and in other embodiments can be omitted. The axial wires 149A, 149B can be made of a structurally robust material, such as stainless steel, and have the flattened or rectangular shape in some embodiments as illustrated. While other shapes are also acceptable, the flattened construction provides more mass and thus an enhanced steerability.

The handle 150 includes a first actuator mechanism 152 for retracting the capsule 112 and a second actuator mechanism 154 for tensioning the pull wire 140. The handle 150 can have any shape or size appropriate for convenient handling by a user. The first actuator mechanism 152 is coupled to the sheath 102, and is generally constructed to provide selective proximal retraction and distal advancement of the sheath 102, and particularly of the capsule 112 attached thereto, relative to the prosthesis 101 held in a radially compressed, delivery state therein for covering and uncovering the prosthesis 101. The first actuator mechanism 152 may assume any construction that is capable of providing the desired sheath actuation functionality, such as those described in U.S. Pat. No. 8,579,963 to Tabor, which is assigned to the same assignee as the present disclosure and which is herein incorporated by reference in its entirety. The second actuator mechanism 154 is coupled to the proximal end 142 of the pull wire 140, and is generally constructed to provide selective proximal retraction and distal advancement of the proximal end 142 of the pull wire 140. Stated another way, the second actuator mechanism is coupled to the proximal end 142 of the pull wire 140 and is constructed to selectively push or pull the pull wire 140. The second actuator mechanism 154 may assume any construction that is capable of providing the desired pull wire actuation functionality, such as those described in U.S. patent application Ser. No. 15/065,938 to Griffin, filed on Mar. 10, 2016, which is assigned to the same assignee as the present disclosure and which is herein incorporated by reference in its entirety.

Figure 1B:
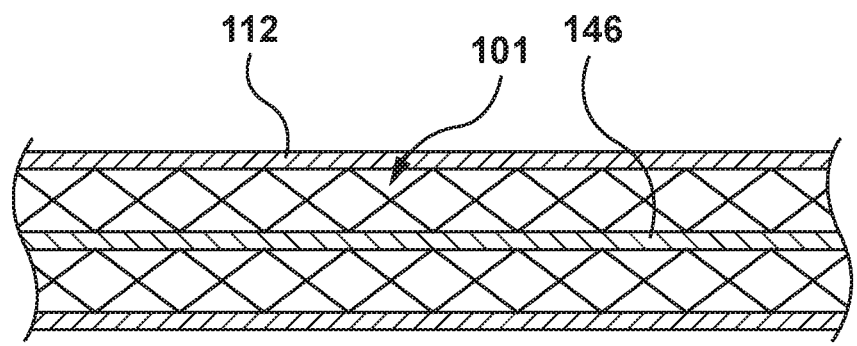
FIG. 1B is a sectional view taken along line B-B of FIG. 1.
Figure 3A:
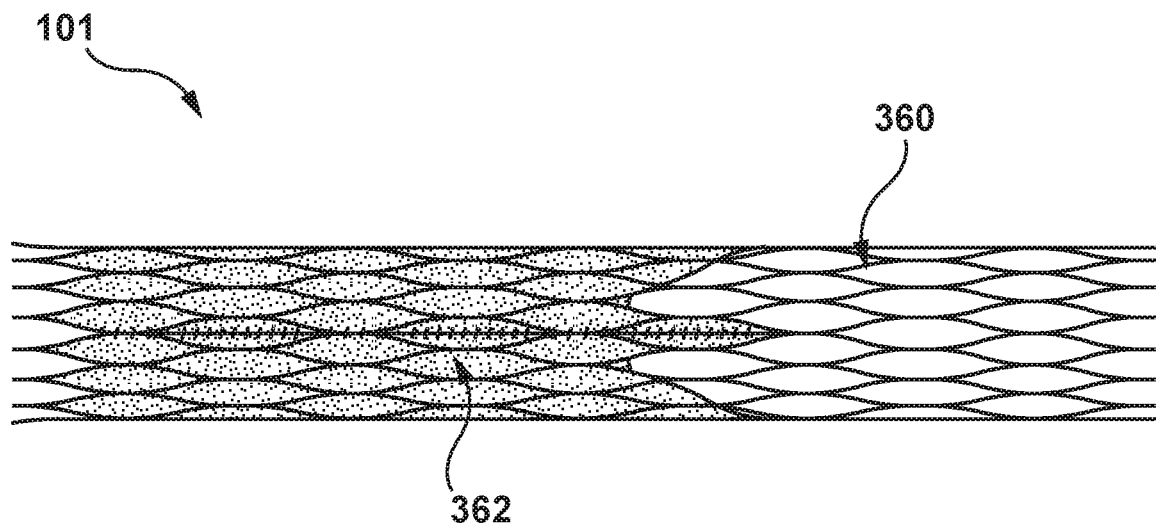
FIG. 3A is a side view of an exemplary heart valve prosthesis of the delivery system of FIG. 1, wherein the heart valve prosthesis is shown in a compressed or delivery configuration.
Figure 3B:
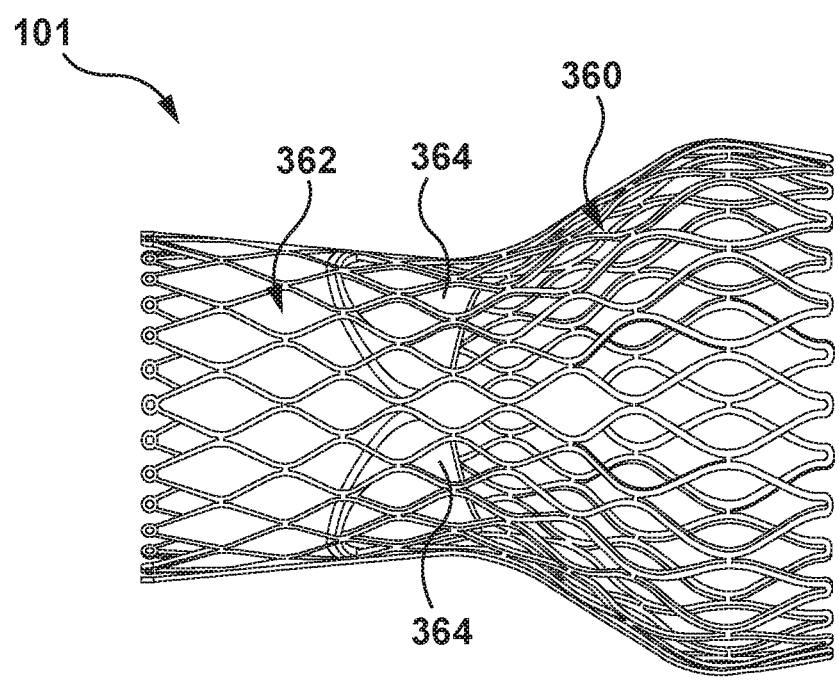
FIG. 3B is a side view of the heart valve prosthesis of FIG. 3A, wherein the heart valve prosthesis is shown in an expanded or deployed configuration.

FIG. 1B is a sectional view taken along line B-B of FIG. 1, and illustrates the prosthesis 101 loaded within the capsule 112 of the delivery device 100. FIG. 3A is a side view of the prosthesis 101 removed from the delivery device 100 and shown in a compressed or delivery configuration, while FIG. 3B is a side view of the prosthesis 101 removed from the delivery device 100 and shown in an expanded or delivery configuration. In general terms, the prosthesis 101 includes a stent-like frame 360 for supporting a valve structure 362, which generally includes two or more leaflets 364. The stent-like frame 360 is a generally tubular support structure having an internal area or lumen within which the valve structure 362 having leaflets 364 will be secured. The valve structure 362 may be constructed from tissue and/or synthetic materials, as would be known to one of ordinary skill in the art. The stent-like frame 360 is constructed from a shape memory material so as to be configured to self-expand or return to the deployed state of FIG. 3B, when released from the capsule 112 of the delivery device 100. In embodiments hereof, any of the heart valve prostheses disclosed in U.S. Pat. Appl. Pub. No. 2014/0222142 to Kovalsky et al. and in U.S. Pat. No. 8,226,710 to Nguyen et al., each of which is incorporated by reference herein in its entirety, may be delivered and deployed by a delivery device as described herein. In addition, the prosthesis 101 may be a prosthetic valve sold under the trade name CoreValve® available from Medtronic CoreValve, LLC. Further, any other heart valve prosthesis may be delivered and deployed using the delivery devices described herein. In the embodiment of FIGS. 3A and 3B, the prosthesis 101 is configured for replacing or repairing an aortic valve. Alternatively, other shapes are also envisioned, adapted to the specific anatomy of the valve to be repaired (e.g., prosthetic heart valves in accordance with the present disclosure can be shaped and/or sized for replacing a native mitral, pulmonic, or tricuspid valve).

Figure 4:
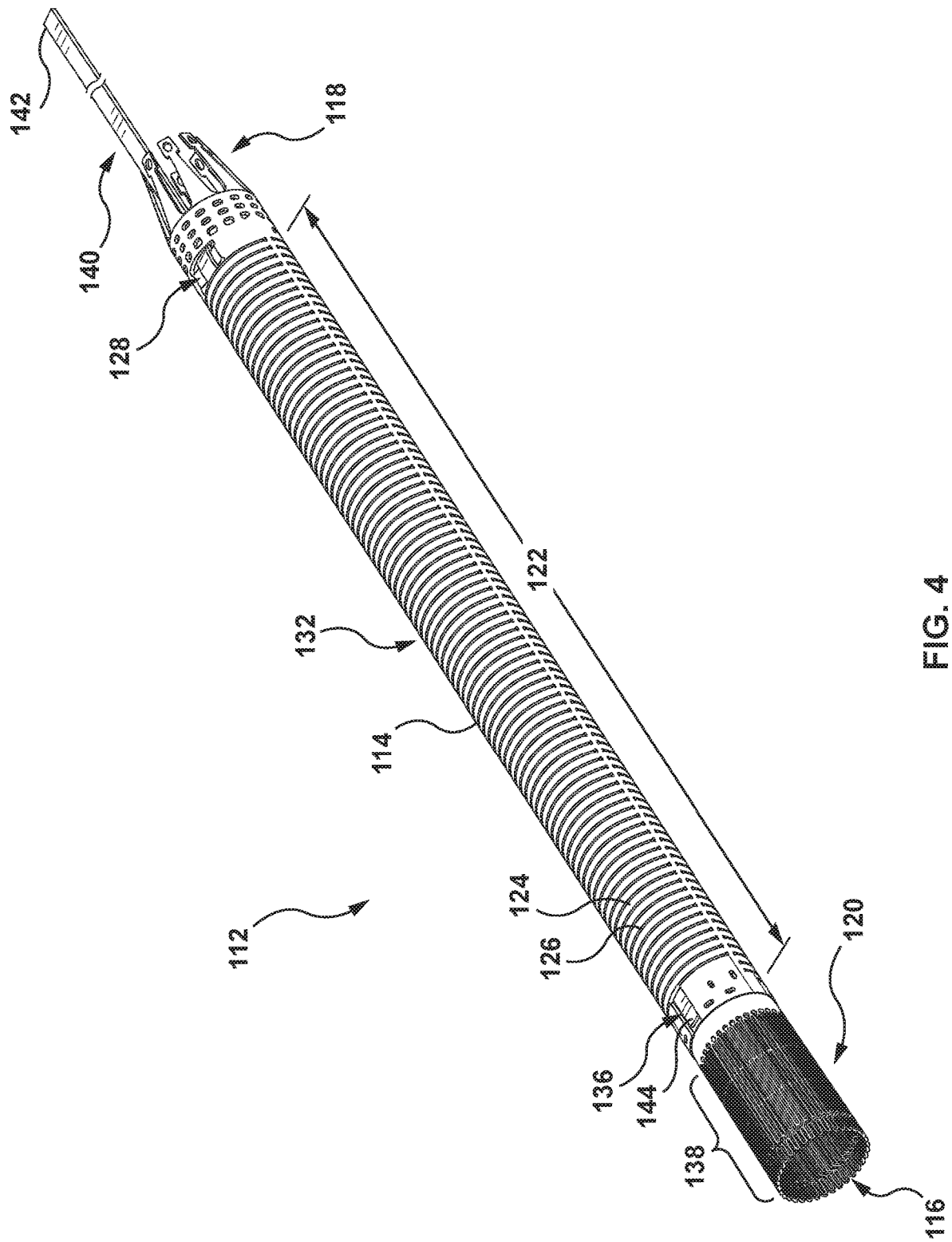
FIG. 4 is a perspective view of the capsule and a pull wire of the delivery system of FIG. 1, wherein the capsule and the pull wire are removed from the remainder of the delivery system for illustrative purposes.

Turning now to FIG. 4, the capsule 112 according to an embodiment hereof will now be described in more detail. FIG. 4 is a perspective view of the capsule 112 and the pull wire 140 removed from the remainder of the delivery system for illustrative purposes. The capsule 112 has a tubular body 114 and includes a proximal end 118 and a distal end 120, and defines a lumen 116 therethrough that is in fluid communication with the central lumen 108 of the sheath 102. An intermediate region 122 of the tubular body 114 includes a plurality of slots 126 separated, or demarcated, by a plurality of ribs 124, such that generally each rib 124 is separated from an adjacent rib 124 by a slot 126. The plurality of ribs 124 and the plurality of slots 126 substantially extend in a circumferential direction around the central longitudinal axis LA of the delivery device 100. The plurality of ribs 124 and the plurality of slots 126 are formed via laser-cutting the tubular body 114 and are configured to impart non-kinking flexibility to the capsule 112 that allows the capsule 112 to bend when the pull wire 140 is selectively tensioned, thereby reducing the pulling force required for bending the capsule 112 and the prosthesis 101 held therein.

Figure 5:
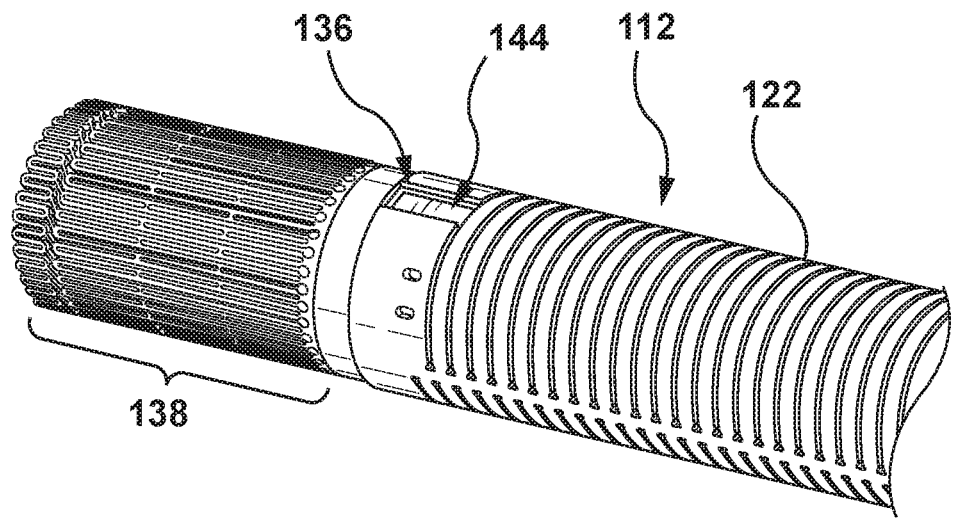
FIG. 5 is an enlarged view of a portion of FIG. 4, wherein an anchor slot of the capsule is shown with the pull wire attached thereto.

As best shown in the enlarged view of FIG. 5, which shows the point of attachment between the pull wire 140 and the capsule 114, the capsule 112 includes an anchor slot 136 formed through the wall of the tubular body 114 of the capsule 112. The distal end 144 of the pull wire 140 is attached or secured to the capsule 112 at the anchor slot 136. The anchor slot 136 is disposed distal to the plurality of ribs 124 and the plurality of slots 126 of the intermediate region 122 of the tubular body 114 of the capsule 112. The anchor slot 136 will be described in more detail herein with respect to FIGS. 9-12.

Figure 6:
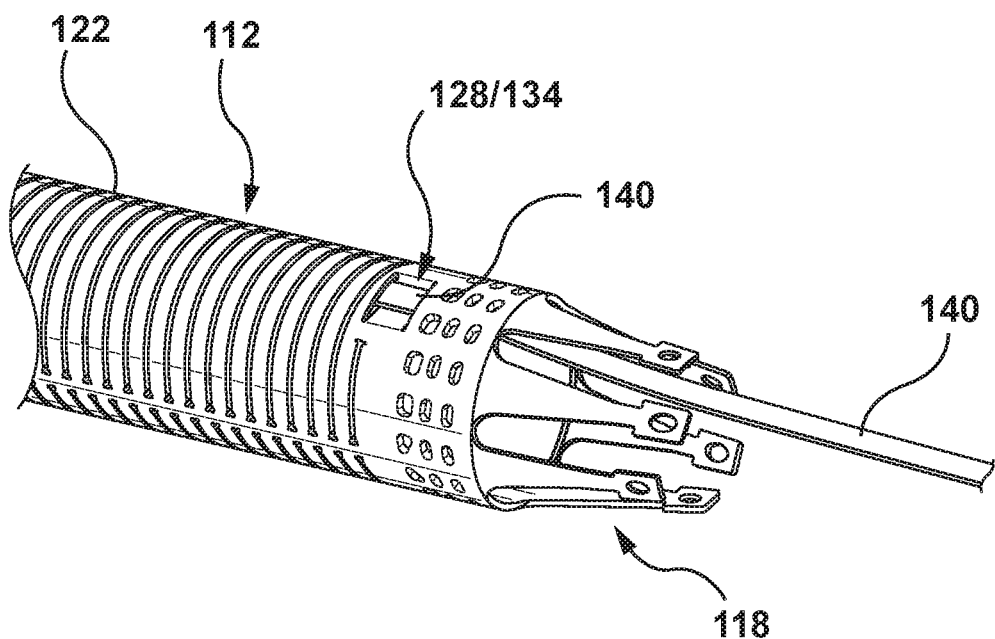
FIG. 6 is an enlarged view of a portion of FIG. 4, wherein an indented segment of the capsule is shown with the pull wire extending thereover.

The pull wire 140 is slidably disposed within the longitudinally-extending lumen 110 of the sheath 102 as described above and is further disposed along an inner surface 130 of the tubular body 114 of the capsule 112. The capsule 112 includes an indented segment 128 defined on the tubular body 114 that is configured to ensure that the pull wire 140 remains flush or taut against the inner surface 130 of the tubular body 114 of the capsule 112. The indented segment 128 is disposed proximal to the plurality of ribs 124 and the plurality of slots 126 of the intermediate region 122 of the tubular body 114 of the capsule 112. The indented segment 128 is an integral portion of the tubular body 114 that is disposed radially inward relative to the reminder of the tubular body 114. FIG. 6 is an enlarged view of a portion of FIG. 4, and illustrates an enlarged view of the indented segment 128 with the pull wire 140 extending thereover. A portion of the pull wire 140 crosses over an outer surface 134 of the indented segment 128. More particularly, the pull wire 140 extends alongside or adjacent to the inner surface 130 of the tubular body 114 proximal to the indented segment 128 and extends alongside or adjacent to the inner surface 130 of the tubular body 114 distal to the indented segment 128. However, the pull wire 140 extends overs the outer surface 134 of the indented segment 128. The indented segment 128 thus holds or secures the pull wire 140 so that it will be flush or taut against the inner surface 130 of the tubular body 114 of the capsule 112. The indented segment 128 will be described in more detail herein with respect to FIGS. 17-23.

Figure 7:
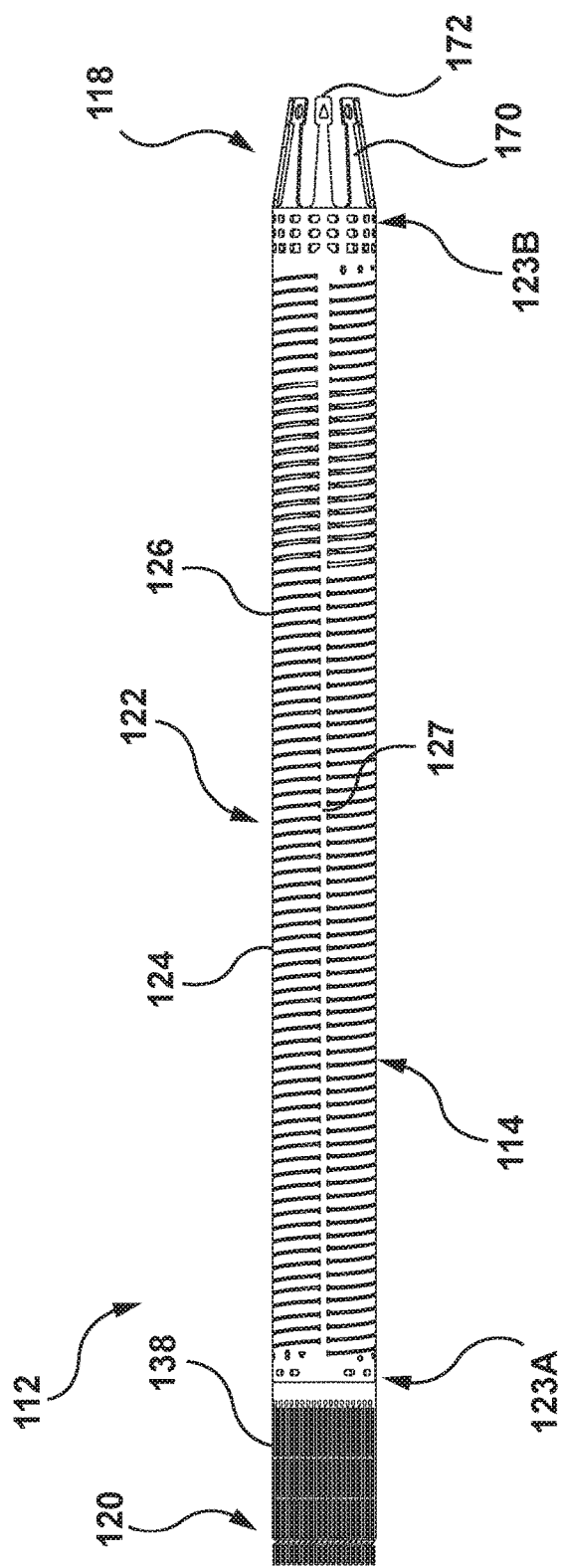
FIG. 7 is a side view of the capsule of the delivery system of FIG. 1, wherein the capsule is removed from the remainder of the delivery system for illustrative purposes and a circumferentially flaring feature of the capsule is shown in a non-flared state.
Figure 8:
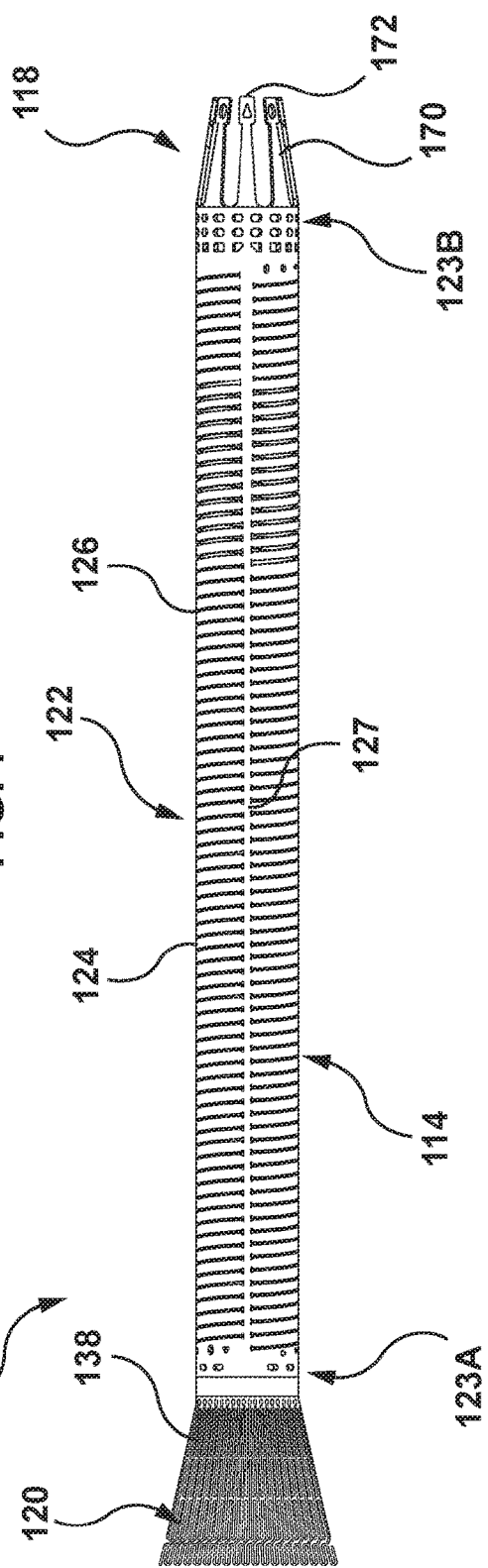
FIG. 8 is a side view of the capsule of the delivery system of FIG. 1, wherein the capsule is removed from the remainder of the delivery system for illustrative purposes and the circumferentially flaring feature of the capsule is shown in a flared state.

The structure of the capsule 112 will now be described in more detail with respect to FIGS. 7 and 8, which illustrate side views of the capsule 112 removed from the remainder of the delivery device 100. The proximal end 118 of the capsule 112 is configured for mounting to the distal end 106 of the sheath 102 and in some constructions includes a plurality of circumferentially-spaced fingers 170, each terminating at a proximal end 172. In some constructions, the proximal end 172 of each of the fingers 170 can have an enlarged width as shown. Regardless, the spaced fingers 170 are readily interposed within (alternatively over) the distal end 106 of the sheath 102 so as to facilitate attachment thereto (e.g., adhesive bond, heated fusing, etc.).

The distal end 120 of the capsule 112 includes a circumferentially flaring feature 138 configured to transition between a normal or non-flared state to a flared state when subjected to an expansion force, and self-transitioning back toward the normal state when the expansion force is removed. In this regard, the circumferentially flaring feature 138 is specifically constructed so as to reduce the force required to recapture a partially-deployed prosthesis 101, while increasing the axial strength and buckling resistance of the capsule 112. In FIG. 7, the circumferentially flaring feature 138 of the capsule is shown in the non-flared state while in FIG. 8, the circumferentially flaring feature 138 of the capsule is shown in the flared state. A diameter of the circumferentially flaring feature 138 is greater in the flared state than in the normal or non-flared state. At least the circumferentially flaring feature 138 of the capsule 112 is formed from a shape memory material such as Nitinol and facilitates repeatable transitioning of the capsule 112 between the non-flared state of FIG. 7 to the flared state of FIG. 8. In this regard, various shape memory materials can be used for the capsule 112, such as a steel, polymers, etc. In some embodiments, the capsule 112 is a Nitinol material, and in particular a Nitinol super elastic material. The circumferentially flaring feature 138 is useful during recapture of the prosthesis 101 during implantation, and is further described in more detail in U.S. Pat. No. 8,562,673 to Yeung et al., which is assigned to the same assignee as the present disclosure and which is herein incorporated by reference in its entirety.

The intermediate region 122 of the tubular body 114 is longitudinally disposed between the proximal end 118 of the capsule 112 and the distal end 120 of the capsule 112. In general terms, the intermediate region 122 incorporates features that impart circumferential or radial rigidity, yet permit or promote transverse articulation, designed to give the capsule 112 adequate axial and radial strength to prevent buckling or kinking. For example, in some embodiments, the capsule 112 includes, along the intermediate region 122, a partial coil or helix-like cut pattern that establishes a plurality of generally circumferentially extending ribs 124. Longitudinally adjacent ones of the ribs 124 are separated by a slot 126. The slots 126 are circumferentially discontinuous, extending less than 180°. As such, slots 126 are helically aligned but are separated from one another. Thus, the cut pattern establishes one or more longitudinal spines 127. With the construction of FIGS. 7 and 8, two of the spines 127 are formed circumferentially opposite one another (it being understood that only one of the spines 127 is visible in FIGS. 7 and 8).

The discontinuous slots 126 and the spines 127 generally connect or maintain adjacent ones of the ribs 124 relative to one another, yet permit transverse articulation so that the capsule 112 is bendable via the pull wire 140. Other constructions that promote desired transverse articulation are also envisioned. While being flexible for requisite bending or articulation (due to a material strength, thickness, and circumferential width), the spines 127 in combination with the ribs 124 provide an enhanced hoop strength attribute to the intermediate region 122, to constrain the prosthesis 101 in the collapsed arrangement as well as longitudinal stability for distally advancing the capsule 112 over a partially deployed (and radially expanded) prosthesis 101. With these and other embodiments, the capsule 112 can be configured to readily identify a location of the spines 127 to a user.

In addition to the plurality of ribs 124 and the plurality of slots 126, the intermediate region 122 of the capsule 112 can include additional one or more reflow zones 123A, 123B. A first reflow zone 123A is disposed between the distal end 120 and the cut pattern of ribs 124/slots 126, and a second reflow zone 123B is disposed between the proximal end 118 and the cut pattern of ribs 124/slots 126. In an embodiment, the capsule 112 may be encapsulated within an inner polymeric layer or liner and an outer polymeric layer or jacket (not shown). The inner and outer polymeric layers are reflowed during manufacture, and the reflow zones 123A, 123B allow reflow material (material of the inner and outer polymeric layers in semi liquid form) to pass therethrough. As a result, the inner and outer polymeric layers fuse or join together during the reflow process in order to encapsulate the capsule 112. In an embodiment, each of the reflow zones 123A, 123B include a plurality of circumferentially spaced apart holes in the form of a ring. In an embodiment, each of the reflow zones 123A, 123B includes at least two rings of circumferentially spaced apart holes. In an embodiment, reflow zone 123A includes exactly two rings of circumferentially spaced apart holes while reflow zone 123B includes exactly three rings of circumferentially spaced apart holes. Further, in an embodiment, the diameter of the holes of the reflow zone 123B are greater or larger than the diameter of the holes of the reflow zone 123A. Other constructions of the reflow zones 123A, 123B are also acceptable, and in some embodiments, one or more of the reflow zones 123A, 123B can be omitted.

Figure 9:
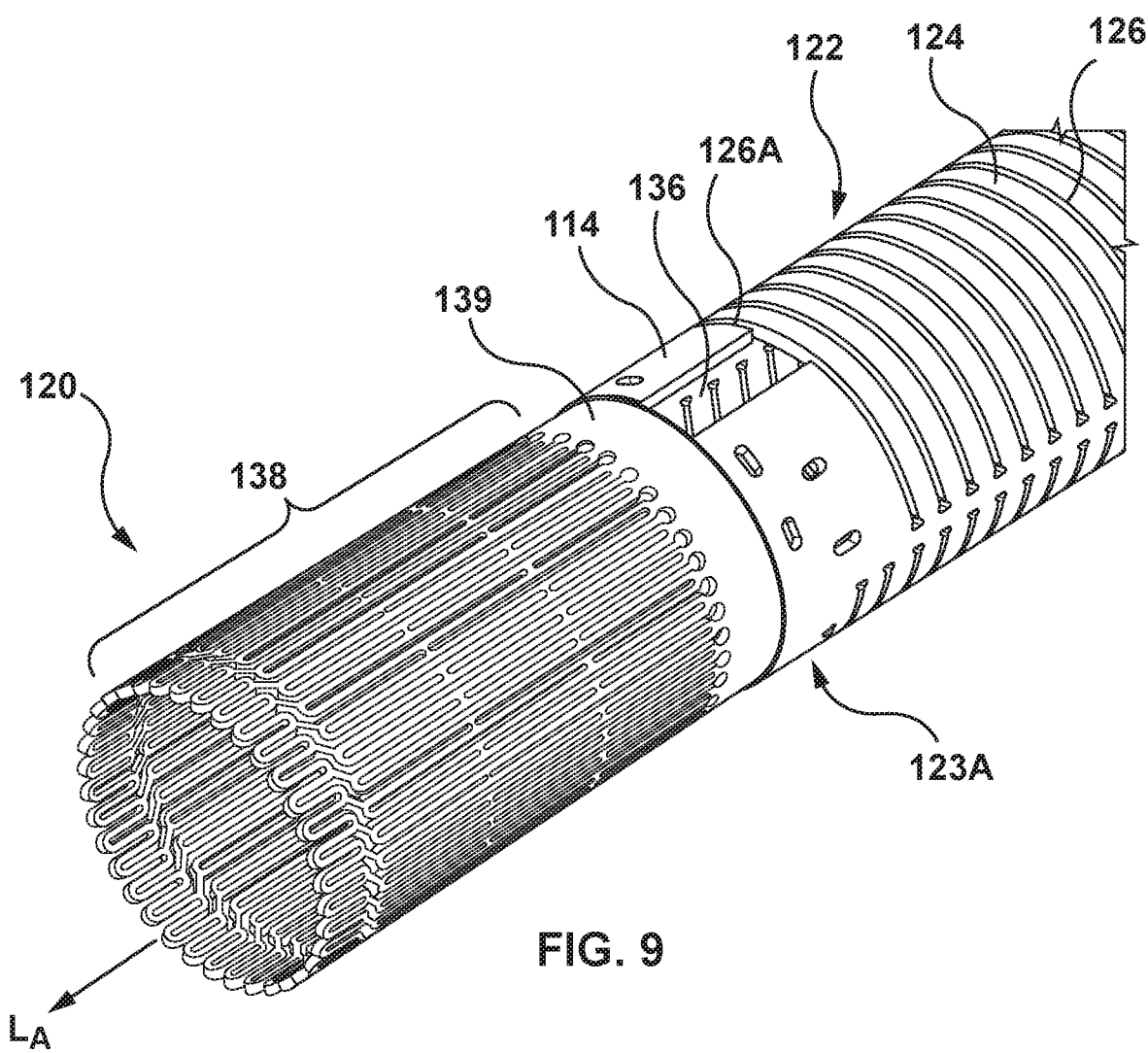
FIG. 9 is an enlarged perspective view of a portion of the capsule of the delivery system of FIG. 1, wherein the capsule is removed from the remainder of the delivery system for illustrative purposes.
Figure 10:
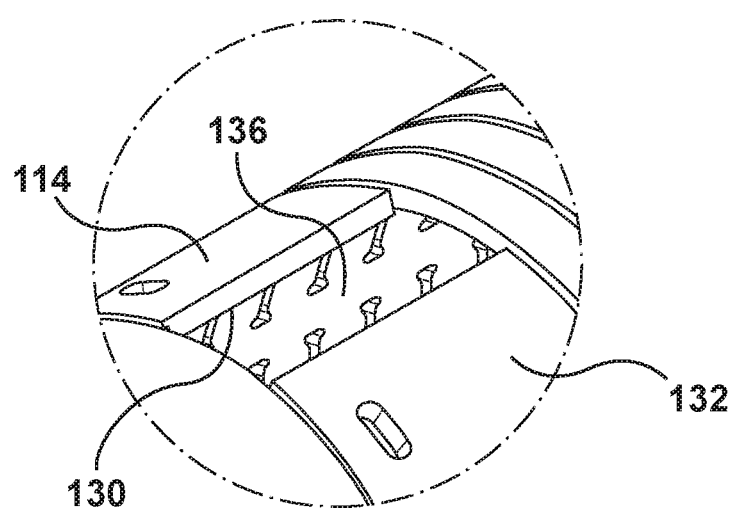
FIG. 10 is an enlarged view of a portion of FIG. 9, wherein an anchor slot of the capsule is shown.
Figure 11:
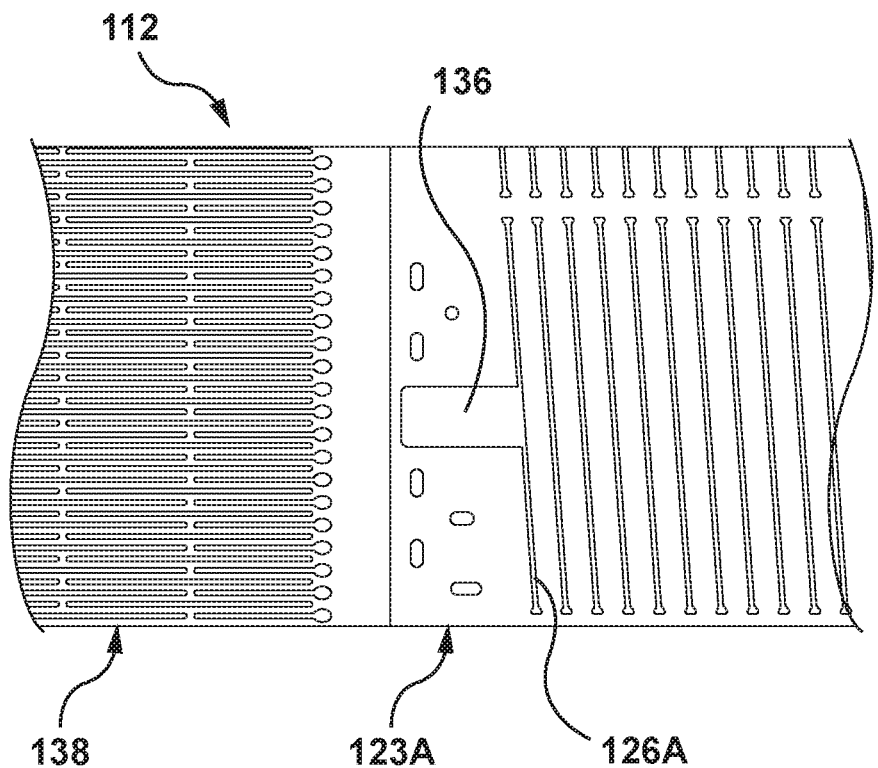
FIG. 11 is a flattened view of the anchor slot of the capsule according to an embodiment hereof.

Turning now to FIGS. 9-11, the anchor slot 136 of the capsule 112 will be described in more detail. FIG. 9 is an enlarged perspective view of a portion of the capsule 112 removed from the remainder of the delivery system for illustrative purposes. FIG. 10 is an enlarged view of a portion of FIG. 9 to clearly illustrate the anchor slot 136. FIG. 11 is a flattened view of the anchor slot 136 of the capsule 112. The anchor slot 136 is an opening or hole formed through the wall of the tubular body 114 of the capsule 112. Stated another way, the anchor slot 136 extends from the outer surface 132 of the tubular body 114 to the inner surface 130 of the tubular body. As previously shown and described with respect to FIG. 5, the anchor slot 136 serves as the point of attachment between the pull wire 140 and the capsule 114 with the distal end 144 of the pull wire 140 being attached or secured to the capsule 112 at the anchor slot 136. In this embodiment, the anchor slot 136 is oblong or rectangular, with the longer length thereof being parallel to a longitudinal axis LA of the capsule 112.

Figure 12:
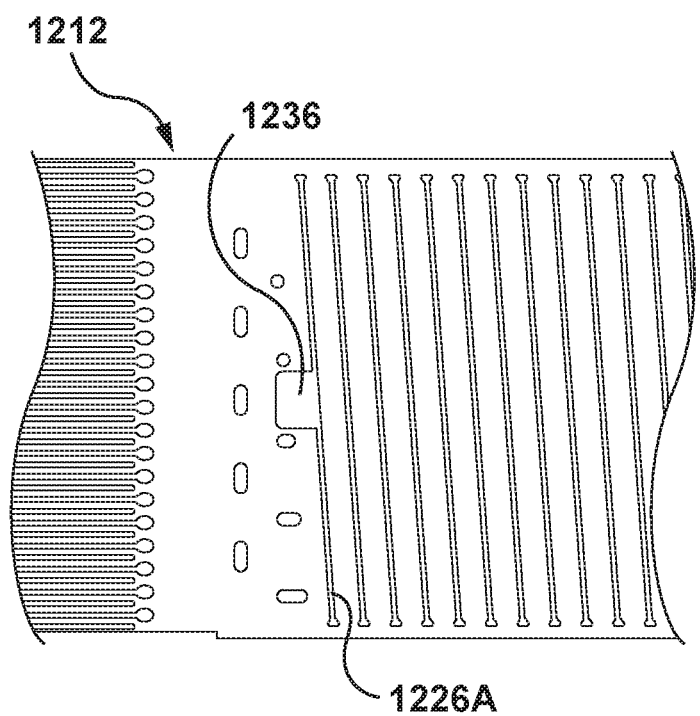
FIG. 12 is a flattened view of the anchor slot of the capsule according to another embodiment hereof.

The anchor slot 136 is disposed on the intermediate region 122 of the tubular body 114 of the capsule 112. As previously stated, the anchor slot 136 is disposed distal to the plurality of ribs 124 and the plurality of slots 126 on the intermediate region 122 of the tubular body 114. Further, the anchor slot 136 is disposed within the reflow zone 123A. The anchor slot 136 extends from a distalmost slot 126A to a proximal end 139 of the circumferentially flaring feature 138. As best shown on the flattened view of FIG. 11, the anchor slot 136 extends over both rings of circumferentially spaced apart holes of the reflow zone 123A. In another embodiment hereof, the anchor slot may be relatively shorter in length so as to not extend over both rings of circumferentially spaced apart holes of the reflow zone 123A. More particularly, FIG. 12 illustrates another embodiment hereof in which an anchor slot 1236 of a capsule 1212 is relatively shorter in length as compared to the anchor slot 136. The anchor slot 1236 extends from a distalmost slot 1226A to the proximalmost ring of circumferentially spaced apart holes of the reflow zone 123A.

Figure 13:
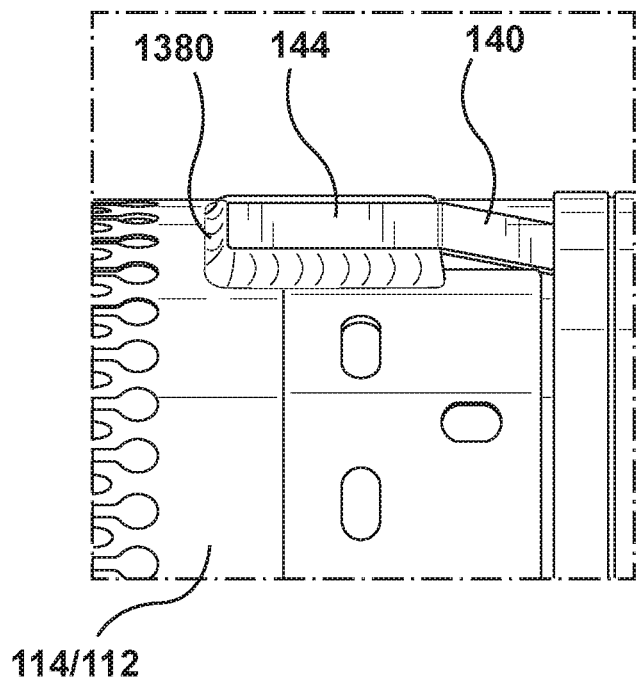
FIG. 13 is a perspective view of the attachment between a distal end of the pull wire and the anchor slot of the capsule according to an embodiment hereof, wherein the attachment includes a weld.
Figure 14:
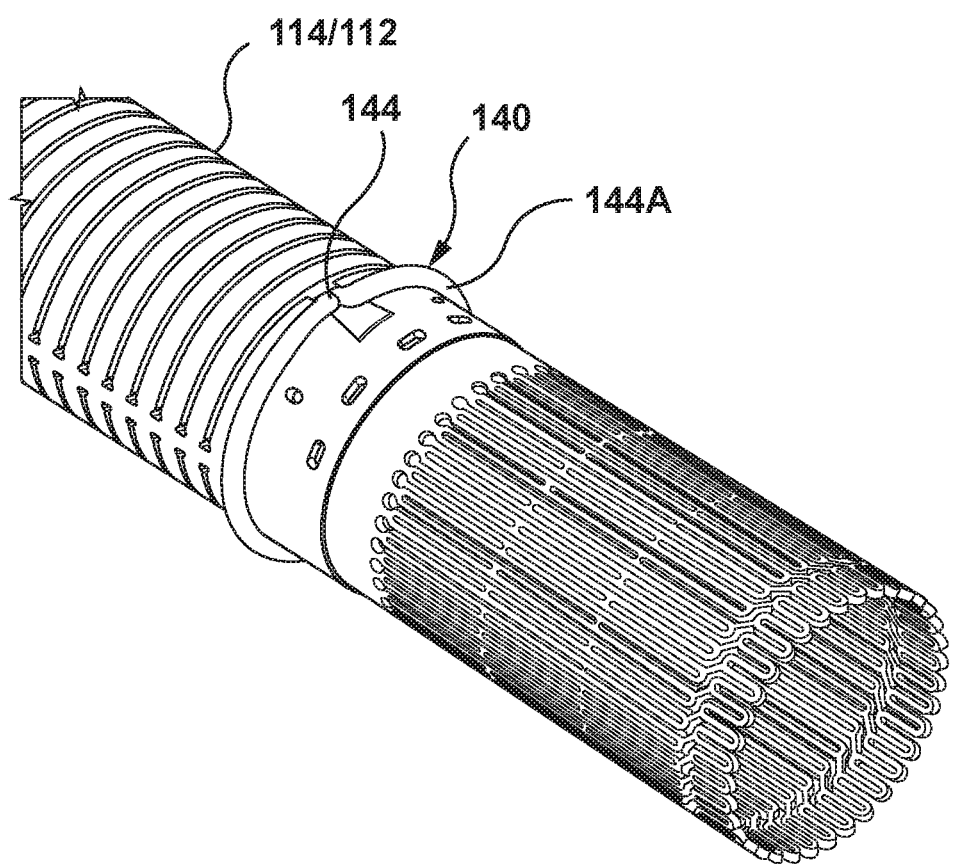
FIG. 14 is a perspective view of the attachment between the distal end of the pull wire and the anchor slot of the capsule according to another embodiment hereof, wherein the attachment includes a loop.
Figure 15:
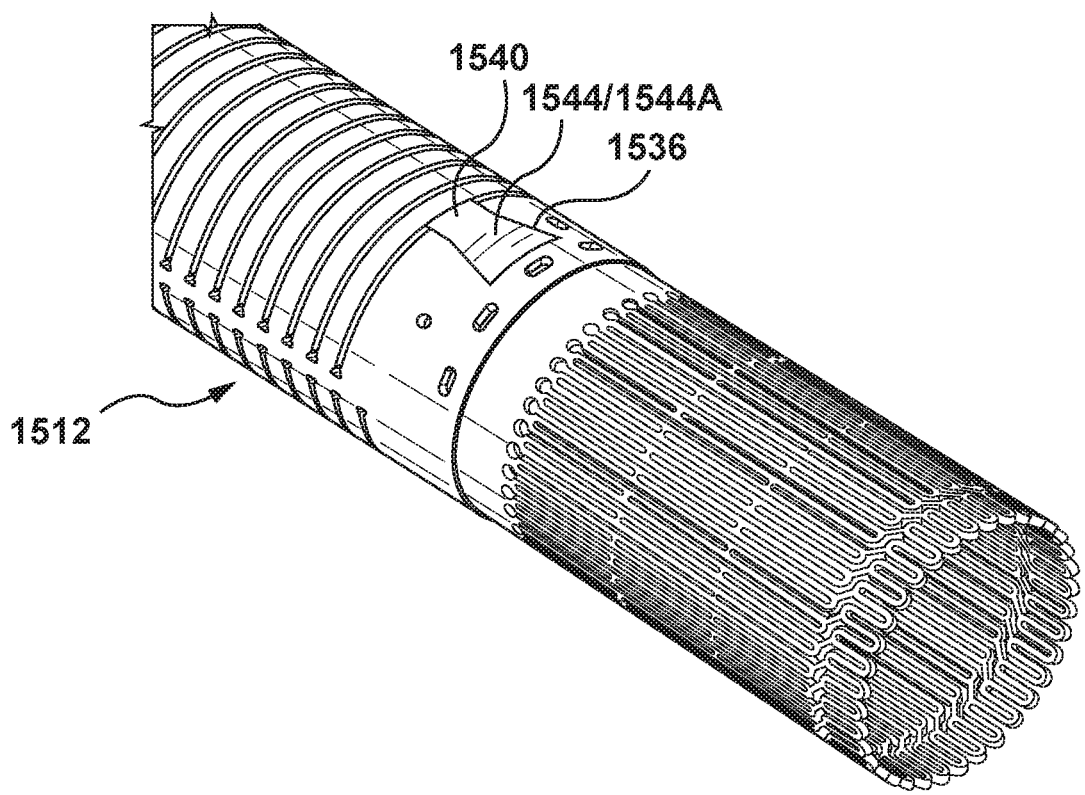
FIG. 15 is a perspective view of the attachment between the distal end of the pull wire and the anchor slot of the capsule according to another embodiment hereof, wherein the attachment includes mating shapes.

The distal end 144 of the pull wire 140 may be attached to the anchor slot 136 using one of several methods of attachment, and it will be understood by one of ordinary skill in the art that the method of attachment depends upon the material of the pull wire 140. For example, in an embodiment depicted in FIG. 13, the pull wire 140 is formed from Nitinol or stainless steel and the distal end 144 of the pull wire 140 is attached to the anchor slot 136 using a weld 1380. Alternatively, the distal end 144 of the pull wire 140 may be attached to the anchor slot 136 using bonding or adhesive. In another embodiment depicted in FIG. 14, the pull wire 140 is formed from KEVLAR or another relatively hard polymeric material. The distal end 144 is wrapped around the outer surface or perimeter of the capsule 112 to form a loop 144A. The distal end 144 may be fed back into the anchor slot 136 and the polymer material of the distal end 144 is reflowed in order to attach the distal end 144 to the loop 144A. Alternatively, a knot (not shown) may be formed in order to attach the polymer material of the distal end 144 to the loop 144A. In another embodiment depicted in FIG. 15, a pull wire 1540 is formed from Nitinol or stainless steel and a distal end 1544 thereof includes a dovetail 1544A. Dovetail 1544A is flared and an anchor slot 1536 of a capsule 1512 has a mating or corresponding shape so that the dovetail 1544A of the distal end 1544 of the pull wire 1540 has an interference fit within the anchor slot 1536. Stated another way, the mating shapes of the anchor slot 1536 and the dovetail 1544A of the distal end 1544 of the pull wire 1540 provide a method of attachment.

Figure 16:
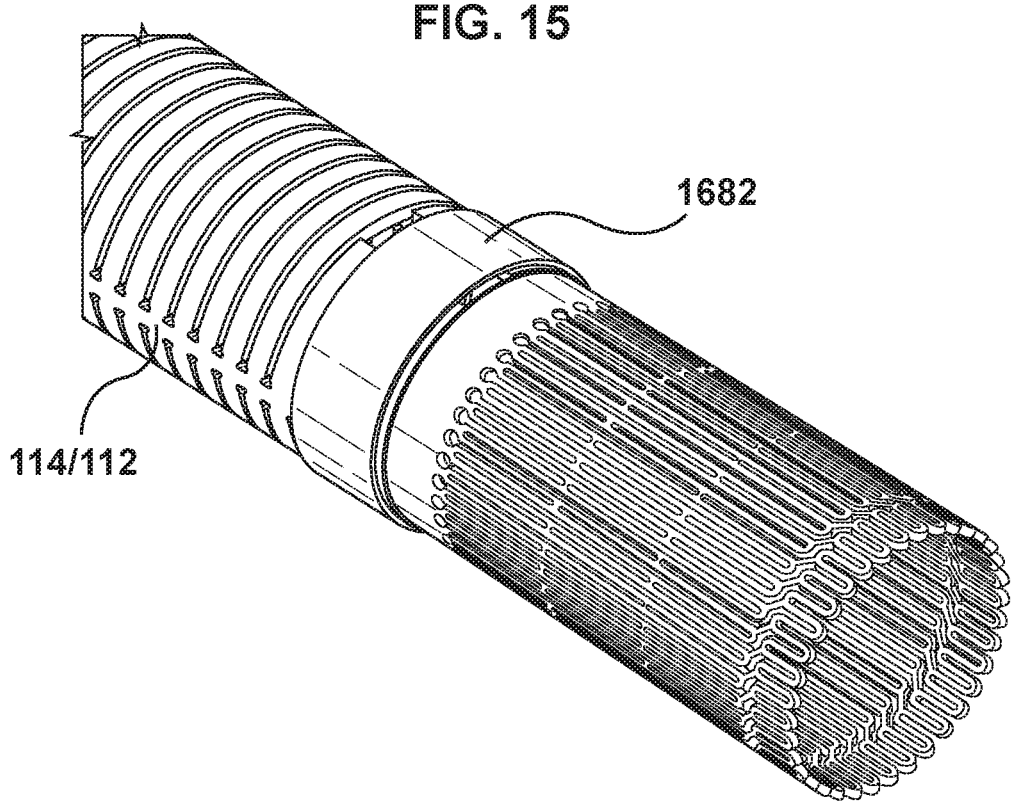
FIG. 16 is a perspective view of the attachment between the distal end of the pull wire and the anchor slot of the capsule according to another embodiment hereof, wherein the attachment includes a metal band.

In an embodiment depicted in FIG. 16, the pull wire 140 (obscured from view in FIG. 16) is formed from stainless steel of Nitinol and a metal band or ring 1682 is utilized to attach the distal end 144 of the pull wire 140 to the capsule 112. The distal end 144 of the pull wire 140 is attached to metal band 1682 by welding. In the embodiment depicted in FIG. 16, the metal band 1682 is a ring of consistent or non-varying width.

Figure 17:
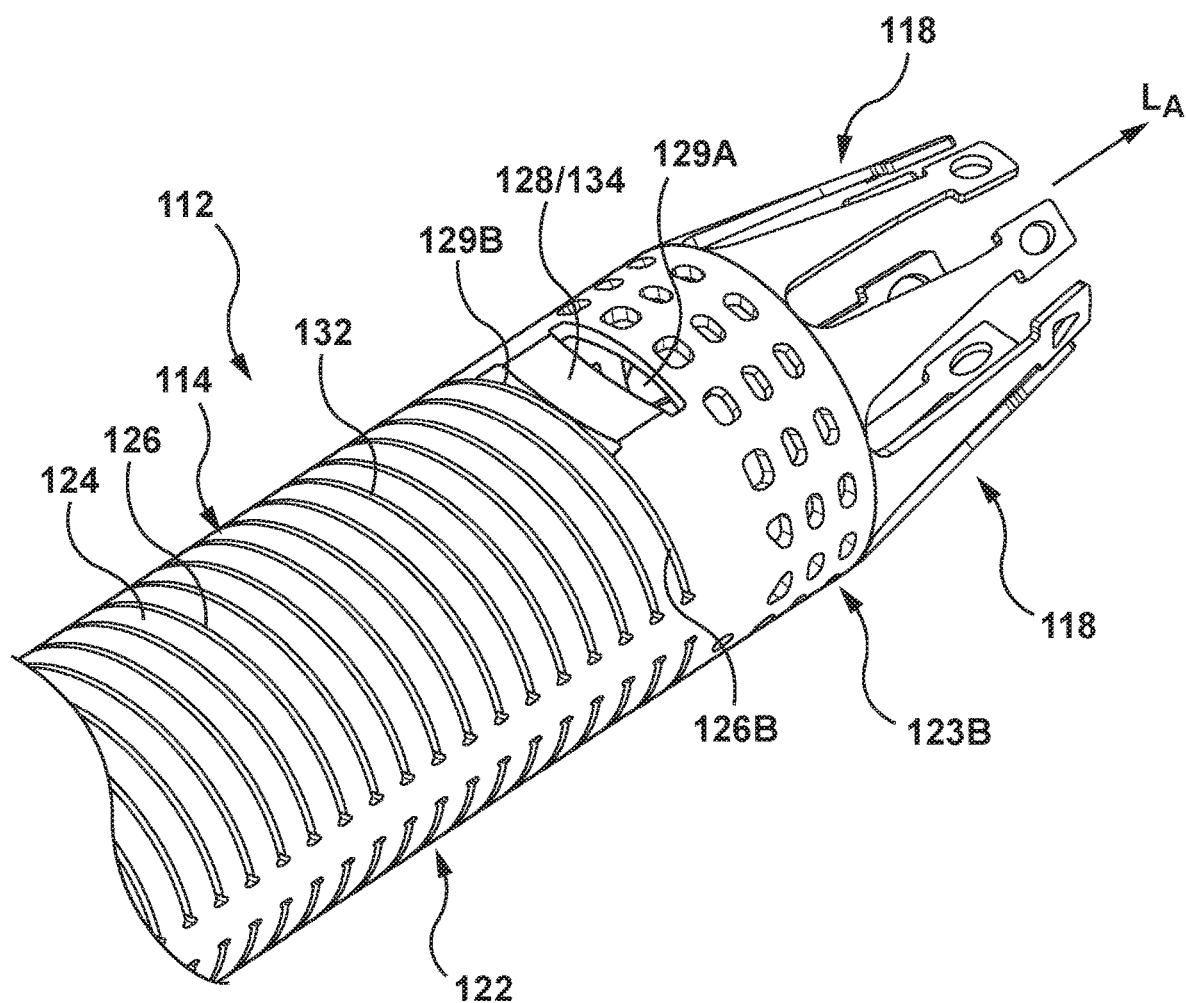
FIG. 17 is an enlarged perspective view of a portion of the capsule of the delivery system of FIG. 1, wherein the capsule is removed from the remainder of the delivery system for illustrative purposes and the indented segment the capsule is shown.
Figure 18:
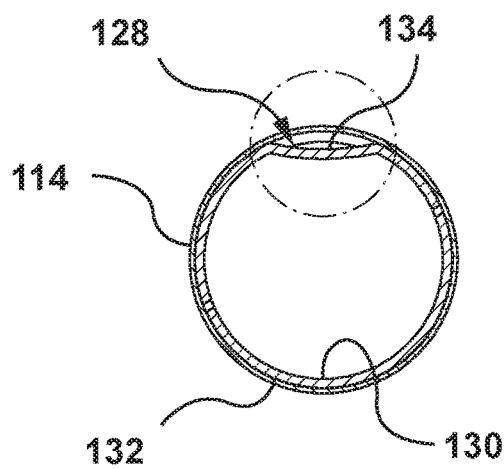
FIG. 18 is a cross-sectional view of the capsule taken through the indented segment of the capsule.
Figure 19:
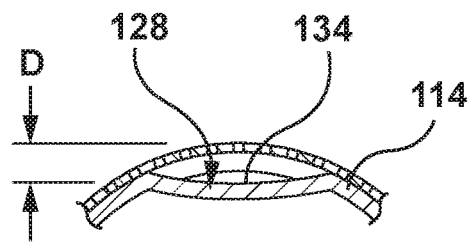
FIG. 19 is an enlarged view of a portion of FIG. 18.
Figure 20:
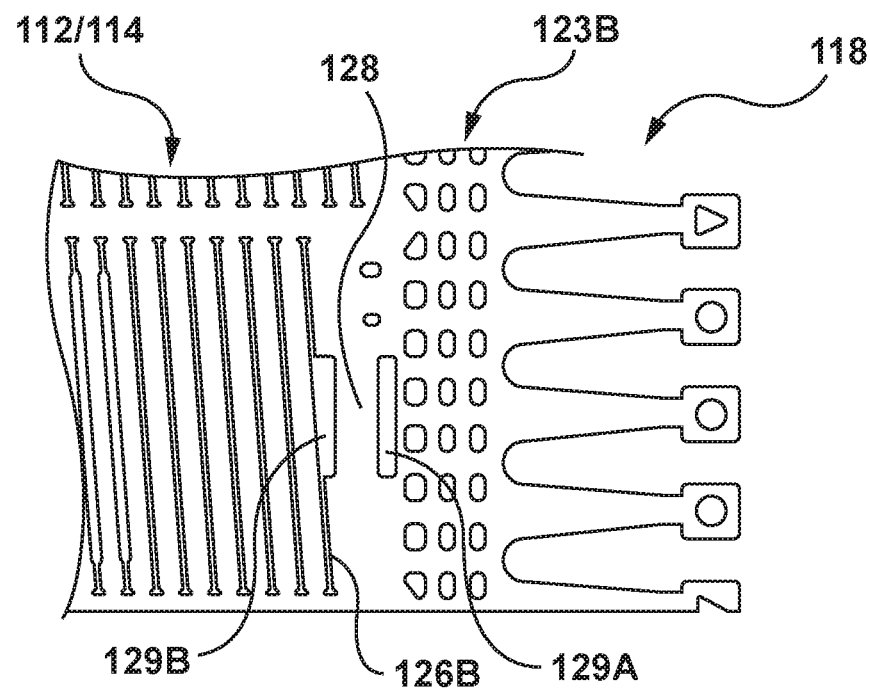
FIG. 20 is a flattened view of the indented segment of the capsule according to an embodiment hereof.

Turning now to FIGS. 17-20, the indented segment 128 will be described in more detail. FIG. 17 is an enlarged perspective view of a portion of the capsule 112 removed from the remainder of the delivery system for illustrative purposes. FIG. 18 is a cross-sectional view of the capsule 112 taken through the indented segment 128, while FIG. 19 is an enlarged view of a portion of FIG. 18 to clearly illustrate the indented segment 128. FIG. 20 is a flattened view of the indented segment 128 of the capsule 112. The indented segment 128 is formed or defined on the tubular body 114 of the capsule 112. The indented segment 128 is an integral portion of the tubular body 114 that is disposed radially inward relative to the reminder of the tubular body 114. More particularly, during manufacture of the capsule 112, two opposing cuts or slots (not shown) are formed on either side the indented segment 128. After the two opposing cuts are formed, force is applied to indent the indented segment 128 so that the indented segment 128 is concave and bows or curves radially inward. The indented segment 128 is then heat set. The indented segment 128 has an indentation depth D as shown on FIG. 19. After formation of the indented segment 128, two opposing radial gaps 129A, 129B extend between the tubular body 114 and the indented segment 128. More particularly, a proximal radial gap 129A extends between the tubular body 114 and a proximal edge of the indented segment 128 and a distal radial gap 129B extends between the tubular body 114 and a distal edge of the indented segment 128. The indentation depth D of the indented segment 128 is greater than a thickness of the pull wire 140 and is configured to permit the pull wire 140 (not shown on FIGS. 17-20) to fit between an inner surface of the tubular body 114 and the outer surface 134 of the indented segment 128. Stated another way, the pull wire 140 is threaded through the two opposing radial gaps 129A, 129B. In this embodiment, the indented segment 128 is oblong or rectangular, with the longer length thereof being perpendicular to a longitudinal axis LA of the capsule 112.

Figure 21:
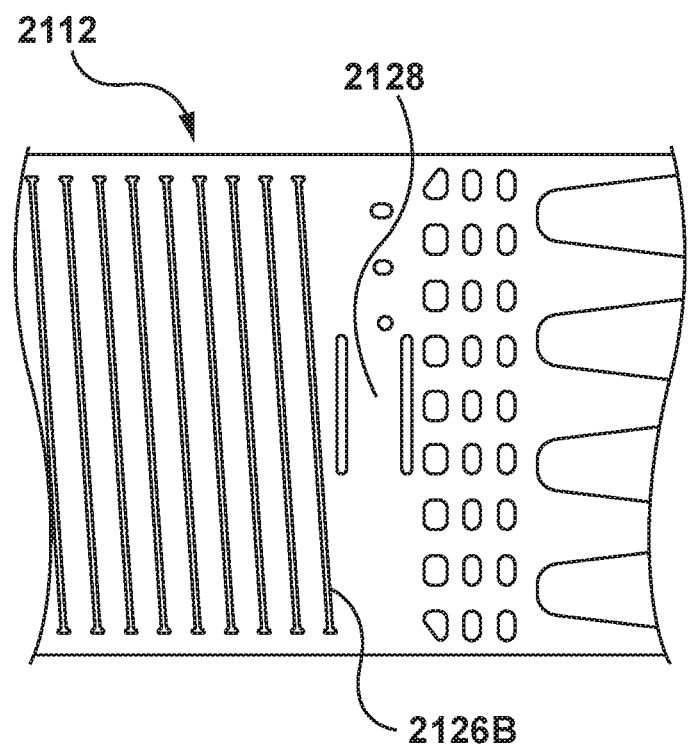
FIG. 21 is a flattened view of the indented segment of the capsule according to another embodiment hereof.

The indented segment 128 is disposed on the intermediate region 122 of the tubular body 114 of the capsule 112. As previously stated, the indented segment 128 is disposed proximal to the plurality of ribs 124 and the plurality of slots 126 on the intermediate region 122 of the tubular body 114. The indented segment 128 extends from a proximalmost slot 126B and is disposed distal to the reflow zone 123B of the intermediate region 122. In the embodiment of FIGS. 17-20, the indented segment 128 is formed to be in fluid communication with the proximalmost slot 126B. In another embodiment hereof, the indented segment is formed spaced apart and proximal to the proximalmost slot. More particularly, FIG. 21 illustrates another embodiment hereof in which an indented segment 2128 of a capsule 2112 is spaced apart from a proximalmost slot 2126B of the capsule 2112.

Figure 22:
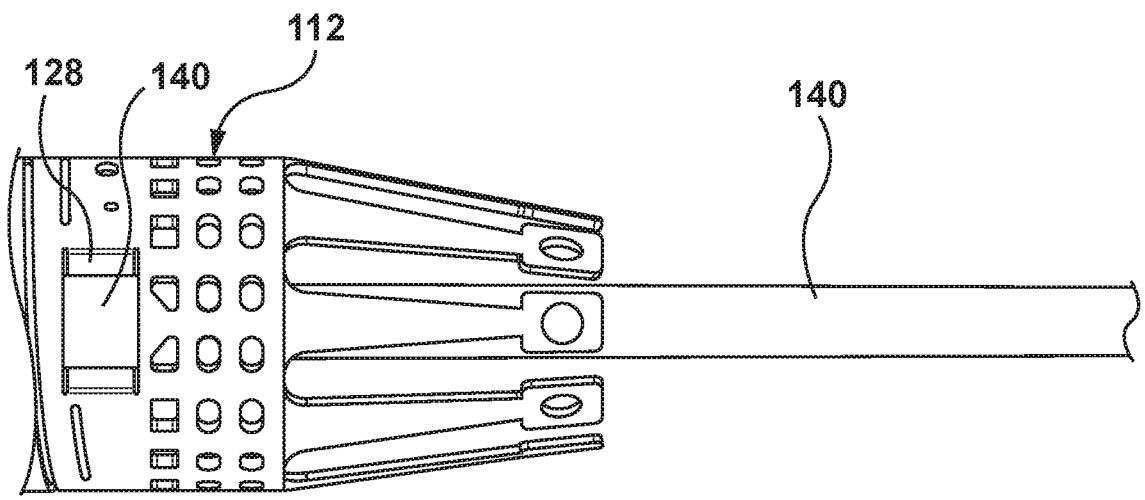
FIG. 22 is a perspective view of the pull wire extending over the indented segment of the capsule.
Figure 23:
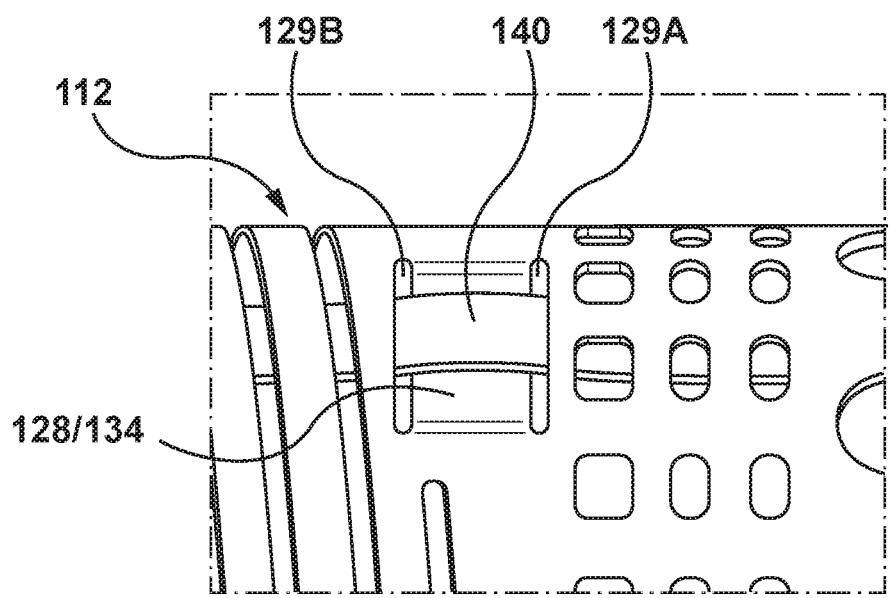
FIG. 23 is an enlarged view of a portion of FIG. 22.

As previously described, the indented segment 128 is configured to ensure that the pull wire 140 remains flush or taut against the inner surface 130 of the tubular body 114 of the capsule 112. FIG. 22 is a perspective view of the pull wire extending over the indented segment of the capsule, while FIG. 23 is an enlarged view of a portion of FIG. 22. The pull wire 140 is slidably disposed within the longitudinally-extending lumen 110 of the sheath 102 as described above and is further disposed along the inner surface 130 of the tubular body 114 of the capsule 112. A portion of the pull wire 140 crosses over an outer surface 134 of the indented segment 128. More particularly, the pull wire 140 is threaded through the radial gaps 129A, 129B such that the pull wire 140 crosses over the indented segment 128 as the pull wire 140 extends from the sheath 102 to the anchor slot 136 of the capsule 112, which is disposed distal to the indented segment 128. The pull wire 140 extends alongside or adjacent to the inner surface 130 of the tubular body 114 proximal to the indented segment 128, extends overs the outer surface 134 of the indented segment 128, and extends alongside or adjacent to the inner surface 130 of the tubular body 114 distal to the indented segment 128. The indented segment 128 thus holds or secures the pull wire 140 so that it will be flush or taut against the inner surface 130 of the tubular body 114 of the capsule 112.

Tension is applied to the pull wire 140 in order to bend the capsule 112 as desired and thereby steer the delivery device 100 within the vasculature as the delivery device 100 is being advanced through the vasculature to the treatment site. For example, the delivery device 100 is manipulated to advance the compressed prosthesis 101 toward the implantation target site in a retrograde manner through a cut-down to the femoral artery, into the patient's descending aorta. The delivery device 100 is then advanced, under fluoroscopic guidance, over the aortic arch, through the ascending aorta, and approximately midway across the defective aortic valve (for an aortic valve replacement procedure). As the delivery device 100 is advanced over the aortic arch, the pull wire 140 is tensioned in order to bend the capsule 112 and steer the delivery device over the aortic arch. Once positioning of the delivery device 100 is complete, the capsule 112 is retracted to deploy the prosthesis 101 to its expanded or deployed state at the treatment site.

As described above, in embodiments hereof, the intermediate region 122 of the tubular body 114 incorporates features that impart circumferential or radial rigidity, yet permit or promote transverse articulation, designed to give the capsule 112 adequate axial and radial strength to prevent buckling or kinking when being bent or curved via tensioning of the pull wire 140 as the capsule 112 is being steered in situ through the vasculature. The capsule 112 includes, along the intermediate region 122, a partial coil or helix-like cut pattern that establishes the plurality of ribs 124, the plurality of slots 126, and two circumferentially opposing longitudinal spines 127. The plurality of ribs 124 of the capsule 112 are shown in embodiments described above as having a uniform pitch. Additional embodiments of the intermediate region of the capsule are contemplated herein with reference to FIGS. 24-35. The embodiments of FIGS. 24-35 have reduced bending stiffness of the capsule while maintaining column stiffness in order to reduce the pull wire load required to steer the capsule, or, will achieve a greater amount of steering for the same pull wire load.

More particularly, a capsule 2412 is shown in FIGS. 24-25. It will be understood that the capsule 2412 is substantially similar to the capsule 112 except for the cut pattern of a plurality of ribs 2424 and a plurality of slots 2426 along an intermediate region 2422 thereof. A proximal end 2418, a distal end 2420, the reflow zones 2423A, 2423B, an anchor slot (not shown in FIGS. 24-25), and an indented segment (not shown in FIGS. 24-25) of the capsule 2412 are the same the proximal end 118, the distal end 120, the reflow zones 123A, 123B, the anchor slot 136, and the indented segment 128 of the capsule 2412 and thus are not described in detail herein.

The intermediate region 2422 of the capsule 2412 includes the plurality of ribs 2424 and the plurality of slots 2426 formed by a partial coil or helix-like cut pattern. Longitudinally adjacent ones of the ribs 2424 are separated by a slot 2426. The slots 2426 are circumferentially discontinuous, extending less than 180°. As such, slots 2426 are helically aligned but are separated from one another. Thus, the cut pattern establishes one or more longitudinal spines 2427. With the construction of FIGS. 24 and 25, two spines 2427 are formed circumferentially opposite one another (it being understood that only one of the spines 2427 is visible in FIGS. 24 and 25). The discontinuous slots 2426 and the spines 2427 generally connect or maintain adjacent ones of the ribs 2424 relative to one another, yet permit transverse articulation so that the capsule 2412 is bendable via a pull wire (not shown in FIGS. 24-25).

The cut pattern of the plurality of ribs 2424 and the plurality of slots 2426 may be considered to include three integral zones or regions including a proximal region 2490, a distal region 2494, and a middle region 2492 extending between the proximal region 2490 and the distal region 2494. The proximal, middle, and distal regions 2490, 2492, 2494, respectively, are clearly shown on FIG. 24. In an embodiment, the proximal region 2490 extends between 5-15% of the total length of the cut pattern, the middle region 2492 extends between 10-25% of the total length of the cut pattern, and the distal region extends between 60-85% of the total length of the cut pattern.

In the embodiment of FIGS. 24-25, a width of the spine 2427 along the distal region 2494 is decreased or reduced relative to a width of the spine 2427 along the proximal region 2492. More particularly, the width of the spine 2427 along the distal region 2494 is $W_1$ and the width of the spine 2427 along the proximal region 2492 is $W_2$, with $W_2$ being approximately twice the size of $W_1$. The width of the spine 2427 along the middle region 2492 gradually tapers from the size of $W_2$ to the size of $W_1$. The width $W_2$ of the spine 2427 along the proximal region 2492 is relatively greater than a width of the spine 127 of the capsule 112.

In addition, in the embodiment of FIGS. 24-25, the middle region 2492 has increased spacing between the plurality of ribs 2424. More particularly, the width of each slot 2426 along the middle region 2492 is increased relative to the width of each slot 2426 along the proximal and distal regions 2490, 2494, respectively. To compensate for the increased widths of the slots 2426 along the middle region 2492, a width of each rib 2424 along the middle region 2492 is decreased relative to the width of each rib 2424 along the proximal and distal regions 2490, 2494, respectively.

FIGS. 26-27 illustrate another embodiment of a capsule 2612. It will be understood that the capsule 2612 is substantially similar to the capsule 112 except for the cut pattern of a plurality of ribs 2624 and a plurality of slots 2626 along an intermediate region 2622 thereof. A proximal end 2618, a distal end 2620, the reflow zones 3023A, 3023B, an anchor slot (not shown in FIGS. 26-27), and an indented segment (not shown in FIGS. 26-27) of the capsule 2612 are the same the proximal end 118, the distal end 120, the reflow zones 123A, 123B, the anchor slot 136, and the indented segment 128 of the capsule 2612 and thus are not described in detail herein.

The intermediate region 2622 of the capsule 2612 includes the plurality of ribs 2624 and the plurality of slots 2626 formed by a partial coil or helix-like cut pattern. Longitudinally adjacent ones of the ribs 2624 are separated by a slot 2626. The slots 2626 are circumferentially discontinuous, extending less than 180°. As such, slots 2626 are helically aligned but are separated from one another. Thus, the cut pattern establishes one or more longitudinal spines 2627. With the construction of FIGS. 26 and 27, two spines 2627 are formed circumferentially opposite one another (it being understood that only one of the spines 2627 is visible in FIGS. 26 and 27). The discontinuous slots 2626 and the spines 2627 generally connect or maintain adjacent ones of the ribs 2624 relative to one another, yet permit transverse articulation so that the capsule 2612 is bendable via a pull wire (not shown in FIGS. 26-27).

The cut pattern of the plurality of ribs 2624 and the plurality of slots 2626 may be considered to include three integral zones or regions including a proximal region 2690, a distal region 2694, and a middle region 2692 extending between the proximal region 2690 and the distal region 2694. The proximal, middle, and distal regions 2690, 2692, 2694, respectively, are clearly shown on FIG. 26. In an embodiment, the proximal region 2690 extends between 5-15% of the total length of the cut pattern, the middle region 2692 extends between 10-25% of the total length of the cut pattern, and the distal region extends between 60-85% of the total length of the cut pattern.

In the embodiment of FIGS. 26-27, the middle region 2692 has increased spacing between the plurality of ribs 2624. More particularly, the width of each slot 2626 along the middle region 2692 is increased relative to the width of each slot 2626 along the proximal and distal regions 2690, 2694, respectively. To compensate for the increased widths of the slots 2626 along the middle region 2692, a width of each rib 2624 along the middle region 2692 is decreased relative to the width of each rib 2624 along the proximal and distal regions 2690, 2694, respectively.

Figure 28:
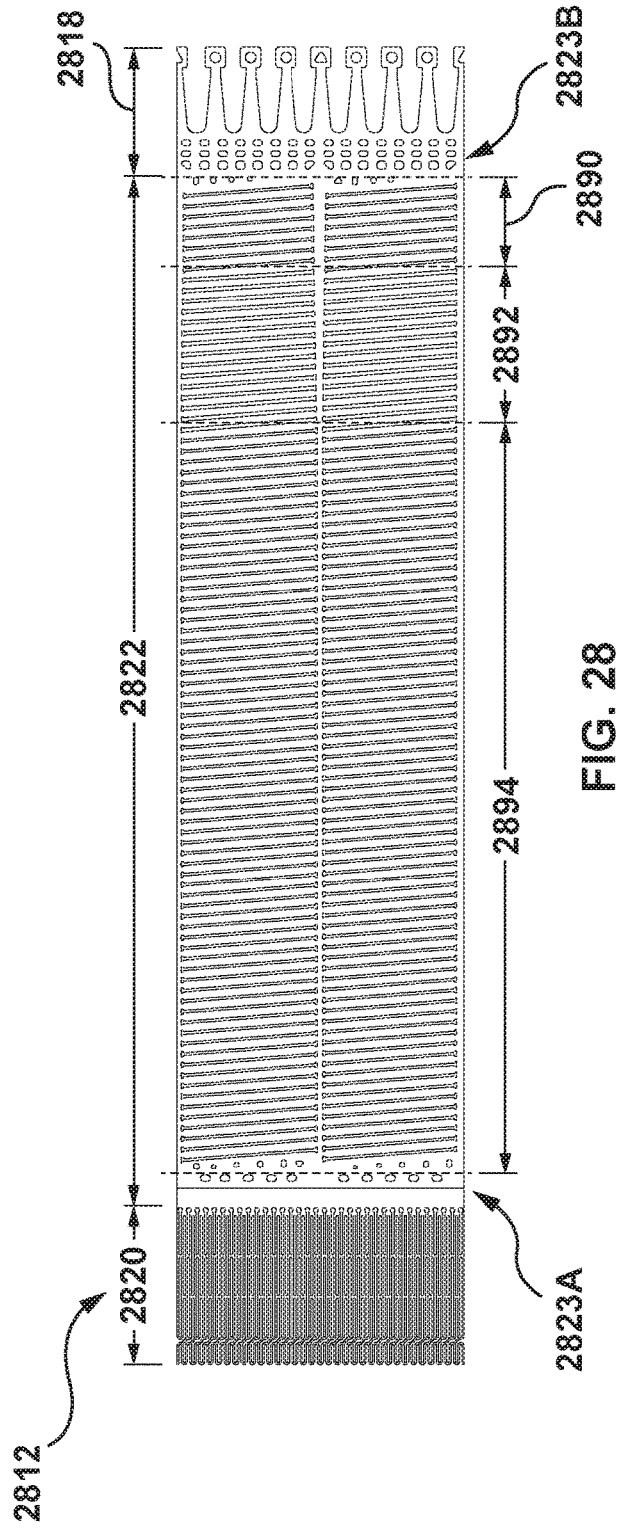
FIG. 28 is a side view of a capsule according to another embodiment hereof, wherein the capsule includes an alternative cut pattern.
Figure 29:
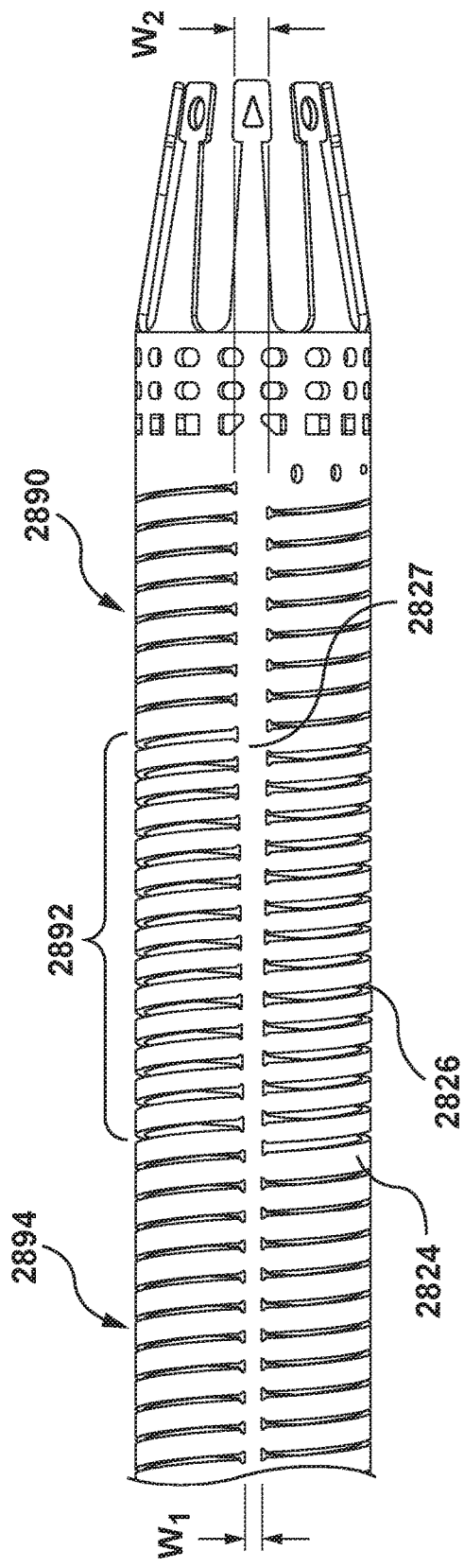
FIG. 29 is a perspective view of a portion of the capsule of FIG. 28.

FIGS. 28-29 illustrate another embodiment of a capsule 2812. It will be understood that the capsule 2812 is substantially similar to the capsule 112 except for the cut pattern of a plurality of ribs 2824 and a plurality of slots 2826 along an intermediate region 2822 thereof. A proximal end 2818, a distal end 2820, the reflow zones 2823A, 2823B, an anchor slot (not shown in FIGS. 28-29), and an indented segment (not shown in FIGS. 28-29) of the capsule 2812 are the same the proximal end 118, the distal end 120, the reflow zones 123A, 123B, the anchor slot 136, and the indented segment 128 of the capsule 2812 and thus are not described in detail herein.

The intermediate region 2822 of the capsule 2812 includes the plurality of ribs 2824 and the plurality of slots 2826 formed by a partial coil or helix-like cut pattern. Longitudinally adjacent ones of the ribs 2824 are separated by a slot 2826. The slots 2826 are circumferentially discontinuous, extending less than 180°. As such, slots 2826 are helically aligned but are separated from one another. Thus, the cut pattern establishes one or more longitudinal spines 2827. With the construction of FIGS. 28 and 29, two spines 2827 are formed circumferentially opposite one another (it being understood that only one of the spines 2827 is visible in FIGS. 28 and 29). The discontinuous slots 2826 and the spines 2827 generally connect or maintain adjacent ones of the ribs 2824 relative to one another, yet permit transverse articulation so that the capsule 2812 is bendable via a pull wire (not shown in FIGS. 28-29).

The cut pattern of the plurality of ribs 2824 and the plurality of slots 2826 may be considered to include three integral zones or regions including a proximal region 2890, a distal region 2894, and a middle region 2892 extending between the proximal region 2890 and the distal region 2894. The proximal, middle, and distal regions 2890, 2892, 2894, respectively, are clearly shown on FIG. 28. In an embodiment, the proximal region 2890 extends between 5-15% of the total length of the cut pattern, the middle region 2892 extends between 10-25% of the total length of the cut pattern, and the distal region extends between 60-85% of the total length of the cut pattern.

In the embodiment of FIGS. 28-29, a width of the spine 2827 along the distal region 2894 is decreased or reduced relative to a width of the spine 2827 along the proximal region 2892. More particularly, the width of the spine 2827 along the distal region 2894 is $W_1$ and the width of the spine 2827 along the proximal region 2892 is $W_2$, with $W_2$ being approximately twice the size of $W_1$. The width of the spine 2827 along the middle region 2892 gradually tapers from the size of $W_2$ to the size of $W_1$. The width $W_2$ of the spine 2827 along the proximal region 2892 is approximately the same as a width of the spine 127 of the capsule 112. In contrast, the width $W_2$ of the spine 2827 of FIGS. 28-29 along the proximal region 2892 is relatively greater than the width of the spine 127 of the capsule 112.

In addition, in the embodiment of FIGS. 28-29, the middle region 2892 has increased spacing between the plurality of ribs 2824. More particularly, the width of each slot 2826 along the middle region 2892 is increased relative to the width of each slot 2826 along the proximal and distal regions 2890, 2894, respectively. To compensate for the increased widths of the slots 2826 along the middle region 2892, a width of each rib 2824 along the middle region 2892 is decreased relative to the width of each rib 2824 along the proximal and distal regions 2890, 2894, respectively.

FIGS. 30-32 illustrate another embodiment of a capsule 3012. It will be understood that the capsule 3012 is substantially similar to the capsule 112 except for the cut pattern of a plurality of ribs 3024 and a plurality of slots 3026 along an intermediate region 3022 thereof. A proximal end 3018, a distal end 3020, the reflow zones 3023A, 3023B, an anchor slot (not shown in FIGS. 30-32), and an indented segment (not shown in FIGS. 30-32) of the capsule 3012 are the same the proximal end 118, the distal end 120, the reflow zones 123A, 123B, the anchor slot 136, and the indented segment 128 of the capsule 3012 and thus are not described in detail herein.

The intermediate region 3022 of the capsule 3012 includes the plurality of ribs 3024 and the plurality of slots 3026 formed by a partial coil or helix-like cut pattern. Longitudinally adjacent ones of the ribs 3024 are separated by a slot 3026. The slots 3026 are circumferentially discontinuous, extending less than 180°. As such, slots 3026 are helically aligned but are separated from one another. Thus, the cut pattern establishes one or more longitudinal spines 3027. With the construction of FIGS. 30-32, two spines 3027 are formed circumferentially opposite one another (it being understood that only one of the spines 3027 is visible in FIGS. 30-32). The discontinuous slots 3026 and the spines 3027 generally connect or maintain adjacent ones of the ribs 3024 relative to one another, yet permit transverse articulation so that the capsule 3012 is bendable via a pull wire (not shown in FIGS. 30-32).

The cut pattern of the plurality of ribs 3024 and the plurality of slots 3026 may be considered to include three integral zones or regions including a proximal region 3090, a distal region 3094, and a middle region 3092 extending between the proximal region 3090 and the distal region 3094. The proximal, middle, and distal regions 3090, 3092, 3094, respectively, are clearly shown on FIG. 30. In an embodiment, the proximal region 3090 extends between 5-15% of the total length of the cut pattern, the middle region 3092 extends between 10-25% of the total length of the cut pattern, and the distal region extends between 60-85% of the total length of the cut pattern.

In the embodiment of FIGS. 30-32, the width of each slot 3026 along the middle region 3092 varies along a length of the slot. The width of each slot 3026 along the middle region 3092 is increased along substantially the full length thereof but tapers at opposing ends 3095A, 3095B thereof towards the spines 3027. Since the width of each slot 3026 along the middle region 3092 is increased, the middle region 3092 has increased spacing between the plurality of ribs 3024. The width of each slot 3026 along the middle region 3092 is increased relative to the width of each slot 3026 along the proximal and distal regions 3090, 3094, respectively. To compensate for the increased widths of the slots 3026 along the middle region 3092, a width of each rib 3024 along the middle region 3092 is decreased relative to the width of each rib 3024 along the proximal and distal regions 3090, 3094, respectively.

In another embodiment hereof depicted in FIGS. 33-35, rather than compensating for the increased slot width with thinner ribs, the middle region may alternatively have a reduced number of ribs. More particularly, a capsule 3312 is shown in FIGS. 33-35. It will be understood that the capsule 3312 is substantially similar to the capsule 112 except for the cut pattern of a plurality of ribs 3324 and a plurality of slots 3326 along an intermediate region 3322 thereof. A proximal end 3318, a distal end 3320, the reflow zones 3323A, 3323B, an anchor slot (not shown in FIGS. 33-35), and an indented segment (not shown in FIGS. 33-35) of the capsule 3312 are the same the proximal end 118, the distal end 120, the reflow zones 123A, 123B, the anchor slot 136, and the indented segment 128 of the capsule 3312 and thus are not described in detail herein.

The intermediate region 3322 of the capsule 3312 includes the plurality of ribs 3324 and the plurality of slots 3326 formed by a partial coil or helix-like cut pattern. Longitudinally adjacent ones of the ribs 3324 are separated by a slot 3326. The slots 3326 are circumferentially discontinuous, extending less than 180°. As such, slots 3326 are helically aligned but are separated from one another. Thus, the cut pattern establishes one or more longitudinal spines 3327. With the construction of FIGS. 33-35, two spines 3327 are formed circumferentially opposite one another (it being understood that only one of the spines 3327 is visible in FIGS. 33-35). The discontinuous slots 3326 and the spines 3327 generally connect or maintain adjacent ones of the ribs 3324 relative to one another, yet permit transverse articulation so that the capsule 3312 is bendable via a pull wire (not shown in FIGS. 33-35).

The cut pattern of the plurality of ribs 3324 and the plurality of slots 3326 may be considered to include three integral zones or regions including a proximal region 3390, a distal region 3394, and a middle region 3392 extending between the proximal region 3390 and the distal region 3394. The proximal, middle, and distal regions 3390, 3392, 3394, respectively, are clearly shown on FIG. 33. In an embodiment, the proximal region 3390 extends between 5-15% of the total length of the cut pattern, the middle region 3392 extends between 10-25% of the total length of the cut pattern, and the distal region extends between 60-85% of the total length of the cut pattern.

In the embodiment of FIGS. 33-35, the width of each slot 3326 along the middle region 3392 varies along a length of the slot. The width of each slot 3326 along the middle region 3392 is increased along substantially the full length thereof but tapers at opposing ends 3395A, 3395B thereof towards the spines 3327. Since the width of each slot 3326 along the middle region 3392 is increased, the middle region 3392 has increased spacing between the plurality of ribs 3324. The width of each slot 3326 along the middle region 3392 is increased relative to the width of each slot 3326 along the proximal and distal regions 3390, 3394, respectively. However, rather than compensating for the increased slot width with thinner ribs as shown in FIGS. 30-32, the middle region 3392 has a reduced number of ribs 3392 compared to the middle region 3092. The width of the ribs 3324 along the middle region 3392 are the same as the width of the ribs 3324 along both the proximal and distal regions 3390, 3394, respectively.

While only some embodiments according to the present invention have been described herein, it should be understood that they have been presented by way of illustration and example only, and not limitation. Various changes in form and detail can be made therein without departing from the spirit and scope of the invention. Further, each feature of each embodiment discussed herein, and of each reference cited herein, can be used in combination with the features of any other embodiment. All patents and publications discussed herein are incorporated by reference herein in their entirety.

What is claimed is:

1. A delivery device comprising:
   a handle;
   a sheath distally extending from the handle, the sheath defining a central lumen there-through and having a longitudinally-extending lumen formed within a wall of the sheath;
   a capsule distally extending from the sheath, the capsule having a tubular body with an intermediate region having a plurality of ribs and a plurality of slots defined therein, wherein the capsule includes an indented segment defined on the tubular body, the indented segment being disposed radially inward relative to the tubular body; and
   a pull wire having a proximal end attached to the handle and a distal end attached to the capsule, wherein the pull wire is tensioned to bend the capsule, and
   wherein the pull wire is slidably disposed within the longitudinally-extending lumen of the sheath and along an inner surface of the tubular body of the capsule with a portion of the pull wire crossing over an outer surface of the indented segment; and
   wherein the indented segment is disposed proximal to the plurality of ribs and the plurality of slots of the intermediate region of the tubular body of the capsule.

2. The delivery device of claim 1, wherein the capsule is configured to retain a prosthesis in a radially compressed state therein.

3. The delivery device of claim 1, wherein the capsule further includes an anchor slot formed through a wall of the tubular body of the capsule, the distal end of the pull wire being attached to the capsule at the anchor slot.

4. The delivery device of claim 3, wherein the anchor slot is disposed distal to the plurality of ribs and the plurality of slots of the intermediate region of the tubular body of the capsule.

5. The delivery device of claim 1, wherein the plurality of ribs and the plurality of slots substantially extend in a circumferential direction around a longitudinal axis of the capsule.

6. The delivery device of claim 1, wherein each rib of the plurality of ribs is separated from an adjacent rib of the plurality of ribs by a slot of the plurality of slots.

7. The delivery device of claim 1, further comprising:
   an inner shaft slidingly disposed within the central lumen of the sheath.

8. The delivery device of claim 1, wherein a proximal end of the capsule is attached to a distal end of the sheath.

9. The delivery device of claim 1, wherein the capsule includes a circumferentially flaring feature configured to transition between a normal state and a flared state, a diameter of the circumferentially flaring feature being greater in the flared state than in the normal state, wherein the capsule includes a shape memory component constructed to naturally assume the normal state.

10. A delivery system for transcatheter delivery of a prosthesis comprising:
    a delivery device including:
       a handle;
       a sheath distally extending from the handle, the sheath defining a central lumen there-through and having a longitudinally-extending lumen formed within a wall of the sheath;
       a capsule distally extending from the sheath, the capsule having a tubular body with an intermediate region having a plurality of ribs and slots defined therein, wherein the capsule includes an indented segment defined on the tubular body, the indented segment being disposed radially inward relative to the tubular body; and
       a pull wire having a proximal end attached to the handle and a distal end attached to the capsule, wherein the pull wire is tensioned to bend the capsule and wherein the pull wire is slidably disposed within the longitudinally-extending lumen of the sheath and along an inner surface of the tubular body of the capsule with a portion of the pull wire crossing over an outer surface of the indented segment; and
    a prosthesis configured to be disposed within the capsule in a radially compressed delivery state and configured to deploy to an expanded state after release from the capsule.

11. The delivery system of claim 10, wherein the indented segment is disposed proximal to the plurality of ribs and the plurality of slots of the intermediate region of the tubular body of the capsule.

12. The delivery system of claim 10, wherein the capsule further includes an anchor slot formed through a wall of the tubular body of the capsule, the distal end of the pull wire being attached to the capsule at the anchor slot.

13. The delivery system of claim 12, wherein the anchor slot is disposed distal to the plurality of ribs and the plurality of slots of the intermediate region of the tubular body of the capsule.

14. The delivery system of claim 10, wherein the plurality of ribs and the plurality of slots substantially extend in a circumferential direction around a longitudinal axis of the capsule.

15. The delivery system of claim 10, wherein each rib of the plurality of ribs is separated from an adjacent rib of the plurality of ribs by a slot of the plurality of slots.

16. The delivery system of claim 10, further comprising:

an inner shaft slidingly disposed within the central lumen of the sheath, wherein the prosthesis is disposed over a distal portion of the inner shaft.

17. The delivery system of claim 10, wherein a proximal end of the capsule is attached to a distal end of the sheath.

18. The delivery system of claim 10, wherein the prosthesis is a prosthetic heart valve.

19. A method of delivering and deploying a prosthesis at a treatment site, the method comprising the steps of:

advancing a delivery system through a vasculature to the treatment site, the delivery system comprising a delivery device and a prosthesis, the delivery device including:

a handle, a sheath distally extending from the handle, the sheath defining a central lumen there-through and having a longitudinally-extending lumen formed within a wall of the sheath, a capsule distally extending from the sheath, the capsule having a tubular body with an intermediate region having a plurality of ribs and a plurality of slots defined therein, wherein the capsule includes an indented segment defined on the tubular body, the indented segment being disposed radially inward relative to the tubular body, wherein the prosthesis is disposed in the capsule in a compressed delivery state, and a pull wire having a proximal end attached to the handle and a distal end attached to the capsule, wherein the pull wire is slidably disposed within the longitudinally-extending lumen of the sheath and along an inner surface of the tubular body of the capsule with a portion of the pull wire crossing over an outer surface of the indented segment;

tensioning of the pull wire in order to bend the capsule; and retracting the capsule to deploy the prosthesis to an expanded deployed state at the treatment site.

* * * * *